(12) United States Patent
Songer et al.

(10) Patent No.: US 8,172,885 B2
(45) Date of Patent: May 8, 2012

(54) BONE PLATE SYSTEM

(75) Inventors: Matthew N. Songer, Marquette, MI (US); Hansen Yuan, Syracuse, NY (US); Thomas S. Kilpela, Marquette, MI (US); Brian P. Janowski, Marquette, MI (US); Gregory A. Berrevoets, Skandia, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1158 days.

(21) Appl. No.: 10/553,940

(22) PCT Filed: Feb. 5, 2004

(86) PCT No.: PCT/US2004/003205
§ 371 (c)(1),
(2), (4) Date: Feb. 2, 2007

(87) PCT Pub. No.: WO2004/071276
PCT Pub. Date: Aug. 26, 2004

(65) Prior Publication Data
US 2007/0123879 A1    May 31, 2007

Related U.S. Application Data

(60) Provisional application No. 60/445,005, filed on Feb. 5, 2003.

(51) Int. Cl.
*A61B 17/60* (2006.01)
(52) U.S. Cl. ........................................ 606/290; 606/289
(58) Field of Classification Search .................. 411/197, 411/248, 272, 273, 35, 354, 531, 533–538, 411/545; 606/280–299, 319, 86 B, 915; *A61B 17/66*
See application file for complete search history.

(56) References Cited

U.S. PATENT DOCUMENTS
434,503 A    8/1890   Corry
(Continued)

FOREIGN PATENT DOCUMENTS
DE    251246    12/1911
(Continued)

OTHER PUBLICATIONS

Moftakhar et al., "Anterior Cervical Plates: A Historical Perspective", Neurosurg Focus 16 (1): Article 8, 2004.
(Continued)

*Primary Examiner* — Eduardo C Robert
*Assistant Examiner* — Lynnsy Schneider
(74) *Attorney, Agent, or Firm* — Fitch, Even, Tabin & Flannery, LLP

(57) ABSTRACT

Bone plate and bone screw lock systems are provided for use in surgical implants. In a preferred form, the bone plate or other implantable member defines a bore for receiving a bone screw and a recess in communication with the bore. A screw lock operates in the bore at the recess to engage and lock the bone screw against unintentional movement. The preferred screw lock is shifted about the screw between an unlocked position to allow manipulation of the screw and a locked position in which the screw lock grips the head of the screw to prevent movement of the screw. The screw lock preferably has a c-shaped collar configuration with opposing ends and a camming engagement with the plate or other member in the recess. Upon rotation of the screw lock, the camming engagement causes the ends of the collar to either shift toward one another in which the collar compresses about the screw to lock the screw or away from another to unlock the screw head.

14 Claims, 10 Drawing Sheets

U.S. PATENT DOCUMENTS

| | | |
|---|---|---|
| 556,642 A | 3/1896 | Reessing |
| 872,897 A | 12/1907 | Chapman et al. |
| 951,800 A | 3/1910 | Center |
| 1,084,680 A | 1/1914 | Wegener |
| 1,087,797 A | 2/1914 | Lowe |
| 1,385,780 A | 7/1921 | Dodds |
| 1,409,157 A | 3/1922 | Dodds |
| 1,756,239 A | 4/1930 | Chojnacki et al. |
| 1,907,506 A | 5/1933 | Coburn |
| 1,980,336 A | 11/1934 | Hoagland |
| 2,248,054 A | 7/1941 | Becker |
| 2,376,768 A * | 5/1945 | Glumer ..................... 411/272 |
| 2,401,856 A | 6/1946 | Brock |
| 2,580,821 A | 1/1952 | Nicola |
| 2,628,838 A | 2/1953 | Smalley |
| 2,780,223 A | 2/1957 | Haggland |
| 2,877,792 A | 3/1959 | Tybus |
| 3,100,516 A | 8/1963 | Naab |
| 3,244,170 A | 4/1966 | McElvenny |
| 3,426,364 A | 2/1969 | Lumb |
| 3,534,731 A | 10/1970 | Mueller |
| 3,596,656 A | 8/1971 | Kaute |
| 3,599,977 A | 8/1971 | Glass et al. |
| 3,659,595 A | 5/1972 | Haboush |
| 3,695,259 A | 10/1972 | Yost |
| 3,741,205 A | 6/1973 | Markolf et al. |
| 3,842,825 A | 10/1974 | Wagner |
| RE28,841 E | 6/1976 | Allgower et al. |
| 4,003,376 A | 1/1977 | McKay et al. |
| 4,029,091 A | 6/1977 | von Bezold et al. |
| 4,334,599 A | 6/1982 | Ritsema et al. |
| RE31,040 E | 9/1982 | Possis |
| 4,361,141 A | 11/1982 | Tanner |
| 4,388,921 A | 6/1983 | Sutter et al. |
| RE31,628 E | 7/1984 | Allgower et al. |
| 4,473,068 A | 9/1984 | Oh |
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Wolfhard et al. |
| 4,599,086 A | 7/1986 | Doty |
| 4,762,122 A | 8/1988 | Slocum |
| 4,771,767 A | 9/1988 | Steffee |
| 4,776,330 A | 10/1988 | Chapman et al. |
| 4,794,918 A | 1/1989 | Wolter |
| 4,890,845 A | 1/1990 | Gatewood |
| 4,892,545 A | 1/1990 | Day et al. |
| 4,904,261 A | 2/1990 | Dove et al. |
| 4,905,679 A | 3/1990 | Morgan |
| 4,943,292 A | 7/1990 | Foux |
| 4,955,908 A | 9/1990 | Frey et al. |
| 4,957,497 A | 9/1990 | Hoogland et al. |
| 4,964,403 A | 10/1990 | Karas et al. |
| 5,002,544 A | 3/1991 | Klaue et al. |
| 5,041,113 A | 8/1991 | Biedermann et al. |
| 5,041,114 A | 8/1991 | Chapman et al. |
| 5,053,036 A | 10/1991 | Perren et al. |
| 5,057,111 A | 10/1991 | Park |
| 5,085,660 A | 2/1992 | Lin |
| 5,092,320 A | 3/1992 | Maurer |
| 5,108,395 A | 4/1992 | Laurain |
| 5,113,685 A | 5/1992 | Asher et al. |
| 5,127,912 A | 7/1992 | Ray et al. |
| 5,127,914 A | 7/1992 | Calderale et al. |
| 5,129,899 A | 7/1992 | Small et al. |
| 5,129,903 A | 7/1992 | Luhr et al. |
| 5,139,498 A | 8/1992 | Astudillo Ley |
| 5,147,360 A | 9/1992 | Dubousset |
| 5,147,361 A | 9/1992 | Ojima et al. |
| 5,151,103 A | 9/1992 | Tepic et al. |
| 5,180,381 A | 1/1993 | Aust et al. |
| 5,190,544 A | 3/1993 | Chapman et al. |
| 5,234,431 A | 8/1993 | Keller |
| 5,261,910 A | 11/1993 | Warden et al. |
| 5,269,784 A | 12/1993 | Mast |
| 5,275,601 A | 1/1994 | Gogolewski et al. |
| 5,304,179 A | 4/1994 | Wagner |
| 5,324,290 A | 6/1994 | Zdeblick et al. |
| 5,326,206 A | 7/1994 | Moore |
| 5,330,535 A | 7/1994 | Moser et al. |
| 5,344,421 A | 9/1994 | Crook |
| 5,346,492 A | 9/1994 | Morgan |
| 5,364,399 A | 11/1994 | Lowery et al. |
| 5,380,323 A | 1/1995 | Howland |
| 5,380,327 A | 1/1995 | Eggers et al. |
| 5,382,248 A | 1/1995 | Jacobson et al. |
| 5,397,363 A | 3/1995 | Gelbard |
| 5,397,364 A | 3/1995 | Kozak et al. |
| 5,415,661 A | 5/1995 | Holmes |
| 5,423,826 A | 6/1995 | Coates et al. |
| 5,454,769 A | 10/1995 | Chen |
| 5,458,641 A | 10/1995 | Ramirez Jimenez |
| 5,468,242 A | 11/1995 | Reisburg |
| 5,478,342 A | 12/1995 | Kohrs |
| 5,486,176 A | 1/1996 | Hildebrand et al. |
| 5,501,684 A | 3/1996 | Schlapfer et al. |
| 5,520,690 A | 5/1996 | Errico et al. |
| 5,520,696 A | 5/1996 | Wenstrom, Jr. |
| 5,522,899 A | 6/1996 | Michelson |
| 5,527,311 A | 6/1996 | Procter et al. |
| 5,531,746 A | 7/1996 | Errico et al. |
| 5,534,027 A | 7/1996 | Hodorek |
| 5,534,032 A | 7/1996 | Hodorek |
| 5,549,612 A | 8/1996 | Yapp et al. |
| 5,569,247 A | 10/1996 | Morrison |
| 5,571,109 A | 11/1996 | Bertagnoli |
| 5,578,034 A | 11/1996 | Estes |
| 5,601,553 A | 2/1997 | Trebing |
| 5,603,713 A | 2/1997 | Aust et al. |
| 5,607,426 A | 3/1997 | Ralph et al. |
| 5,607,428 A | 3/1997 | Lin |
| 5,616,144 A | 4/1997 | Yapp et al. |
| 5,620,443 A | 4/1997 | Gertzbein et al. |
| 5,626,449 A * | 5/1997 | McKinlay ..................... 411/149 |
| 5,643,265 A | 7/1997 | Errico et al. |
| 5,647,872 A | 7/1997 | Gilbert et al. |
| 5,651,651 A | 7/1997 | Spencer |
| 5,653,708 A | 8/1997 | Howland |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,683,465 A | 11/1997 | Shinn et al. |
| 5,690,631 A | 11/1997 | Duncan et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,725,588 A | 3/1998 | Errico et al. |
| 5,731,275 A | 3/1998 | Prevost et al. |
| 5,735,850 A | 4/1998 | Baumgartner et al. |
| 5,735,853 A | 4/1998 | Olerud |
| 5,735,899 A | 4/1998 | Schwartz et al. |
| 5,741,258 A | 4/1998 | Klaue et al. |
| 5,766,176 A | 6/1998 | Duncan |
| 5,766,254 A | 6/1998 | Gelbard |
| 5,797,912 A | 8/1998 | Runciman et al. |
| 5,800,433 A | 9/1998 | Benzel et al. |
| 5,807,396 A | 9/1998 | Raveh |
| 5,810,823 A | 9/1998 | Klaue et al. |
| 5,814,048 A | 9/1998 | Morgan |
| 5,827,285 A | 10/1998 | Bramlet |
| 5,840,078 A | 11/1998 | Yerys |
| 5,843,082 A | 12/1998 | Yuan et al. |
| 5,876,402 A | 3/1999 | Errico et al. |
| 5,879,389 A | 3/1999 | Koshino |
| 5,888,221 A | 3/1999 | Gelbard |
| 5,904,683 A | 5/1999 | Pohndorf et al. |
| 5,916,200 A | 6/1999 | Eppley et al. |
| 5,951,557 A | 9/1999 | Luter |
| 5,951,558 A | 9/1999 | Fiz |
| 5,954,722 A | 9/1999 | Bono |
| 5,964,762 A | 10/1999 | Biedermann et al. |
| 5,976,141 A | 11/1999 | Haag et al. |
| 5,980,540 A | 11/1999 | Bruce |
| 5,984,924 A | 11/1999 | Asher et al. |
| 6,017,345 A | 1/2000 | Richelsoph |

| Patent No. | Kind | Date | Name | Ref |
|---|---|---|---|---|
| 6,022,350 | A | 2/2000 | Ganem | |
| 6,030,389 | A | 2/2000 | Wagner et al. | |
| 6,036,693 | A | 3/2000 | Yuan et al. | |
| 6,039,740 | A | 3/2000 | Olerud | |
| 6,090,111 | A | 7/2000 | Nichols | |
| 6,106,557 | A | 8/2000 | Robioneck et al. | |
| 6,117,173 | A | 9/2000 | Taddia et al. | |
| 6,129,730 | A | 10/2000 | Bono et al. | |
| 6,139,550 | A | 10/2000 | Michelson | |
| 6,152,927 | A | 11/2000 | Farris et al. | |
| 6,159,213 | A | 12/2000 | Rogozinski | |
| 6,183,476 | B1 | 2/2001 | Gerhardt et al. | |
| 6,193,720 | B1 | 2/2001 | Yuan | |
| 6,193,721 | B1 | 2/2001 | Michelson | |
| 6,206,881 | B1 | 3/2001 | Frigg et al. | |
| 6,206,882 | B1 | 3/2001 | Cohen | |
| 6,214,005 | B1 | 4/2001 | Benzel et al. | |
| 6,224,602 | B1 | 5/2001 | Hayes | |
| 6,228,085 | B1 | 5/2001 | Theken et al. | |
| 6,235,032 | B1 | 5/2001 | Link | |
| 6,235,033 | B1 | 5/2001 | Brace et al. | |
| 6,235,034 | B1 | 5/2001 | Bray | |
| 6,241,731 | B1 | 6/2001 | Fiz | |
| 6,254,603 | B1 | 7/2001 | Gertzbein et al. | |
| 6,257,593 | B1 | 7/2001 | White | |
| 6,258,089 | B1 | 7/2001 | Campbell et al. | |
| 6,261,042 | B1 | 7/2001 | Pratt | |
| 6,261,291 | B1 | 7/2001 | Talaber et al. | |
| 6,273,889 | B1 | 8/2001 | Richelsoph | |
| 6,280,445 | B1 | 8/2001 | Morrison et al. | |
| 6,290,703 | B1 | 9/2001 | Ganem | |
| 6,293,949 | B1 | 9/2001 | Justis et al. | |
| D449,692 | S | 10/2001 | Michelson | |
| 6,306,136 | B1 | 10/2001 | Baccelli | |
| 6,306,139 | B1 | 10/2001 | Fuentes | |
| 6,315,779 | B1 | 11/2001 | Morrison et al. | |
| 6,322,562 | B1 | 11/2001 | Wolter | |
| 6,328,738 | B1 | 12/2001 | Suddaby | |
| 6,331,179 | B1 | 12/2001 | Freid et al. | |
| 6,332,887 | B1 | 12/2001 | Knox | |
| 6,342,055 | B1 | 1/2002 | Eisermann et al. | |
| 6,342,057 | B1 | 1/2002 | Brace et al. | |
| 6,361,537 | B1 | 3/2002 | Anderson | |
| 6,364,880 | B1 | 4/2002 | Michelson | |
| 6,379,364 | B1 | 4/2002 | Brace et al. | |
| 6,381,806 | B1 | 5/2002 | Stanesic et al. | |
| 6,383,186 | B1 | 5/2002 | Michelson | |
| 6,398,783 | B1 | 6/2002 | Michelson | |
| 6,402,206 | B1 * | 6/2002 | Simmons et al. | 285/321 |
| 6,402,755 | B1 | 6/2002 | Pisharodi | |
| 6,402,756 | B1 | 6/2002 | Ralph et al. | |
| 6,402,759 | B1 | 6/2002 | Strong et al. | |
| 6,406,478 | B1 | 6/2002 | Kuo | |
| 6,413,259 | B1 | 7/2002 | Lyons et al. | |
| 6,416,528 | B1 | 7/2002 | Michelson | |
| 6,423,068 | B1 | 7/2002 | Reisberg et al. | |
| 6,428,542 | B1 | 8/2002 | Michelson | |
| 6,454,769 | B2 * | 9/2002 | Wagner et al. | 606/279 |
| 6,454,771 | B1 | 9/2002 | Michelson | |
| 6,458,133 | B1 | 10/2002 | Lin | |
| 6,471,704 | B2 | 10/2002 | Gertzbein et al. | |
| 6,478,797 | B1 | 11/2002 | Paul | |
| 6,503,250 | B2 | 1/2003 | Paul | |
| 6,527,776 | B1 | 3/2003 | Michelson | |
| 6,533,786 | B1 | 3/2003 | Needham et al. | |
| 6,572,619 | B2 | 6/2003 | Santilli | |
| 6,575,975 | B2 | 6/2003 | Brace et al. | |
| 6,579,290 | B1 | 6/2003 | Hardcastle et al. | |
| 6,585,769 | B1 | 7/2003 | Muhanna et al. | |
| 6,592,586 | B1 | 7/2003 | Michelson | |
| 6,595,993 | B2 | 7/2003 | Donno et al. | |
| 6,599,290 | B2 | 7/2003 | Bailey et al. | |
| 6,602,255 | B1 | 8/2003 | Campbell et al. | |
| 6,602,256 | B1 | 8/2003 | Hayes | |
| 6,602,257 | B1 | 8/2003 | Thramann | |
| 6,605,090 | B1 | 8/2003 | Trieu et al. | |
| 6,613,053 | B1 | 9/2003 | Collins et al. | |
| 6,613,728 | B1 | 9/2003 | Sirianni et al. | |
| 6,616,666 | B1 | 9/2003 | Michelson | |
| 6,620,163 | B1 | 9/2003 | Michelson | |
| 6,623,486 | B1 | 9/2003 | Weaver et al. | |
| 6,626,907 | B2 | 9/2003 | Campbell et al. | |
| 6,627,590 | B1 | 9/2003 | Sherry et al. | |
| 6,652,525 | B1 | 11/2003 | Assaker et al. | |
| 6,663,632 | B1 | 12/2003 | Frigg | |
| 6,669,700 | B1 | 12/2003 | Farris et al. | |
| 6,692,503 | B2 | 2/2004 | Foley et al. | |
| 6,695,846 | B2 * | 2/2004 | Richelsoph et al. | 606/71 |
| 6,755,833 | B1 | 6/2004 | Paul et al. | |
| 6,780,186 | B2 * | 8/2004 | Errico et al. | 606/71 |
| D501,231 | S | 1/2005 | Rom | |
| 6,860,883 | B2 | 3/2005 | Janowski et al. | |
| 6,890,334 | B2 | 5/2005 | Brace et al. | |
| 6,916,320 | B2 | 7/2005 | Michelson | |
| 6,964,664 | B2 | 11/2005 | Freid et al. | |
| 6,966,735 | B1 * | 11/2005 | Yamazaki | 411/149 |
| 7,048,739 | B2 | 5/2006 | Konieczynski et al. | |
| 7,074,221 | B2 | 7/2006 | Michelson | |
| 7,273,481 | B2 | 9/2007 | Lombardo et al. | |
| 7,410,496 | B2 | 8/2008 | Derouet | |
| 7,452,370 | B2 | 11/2008 | Anderson | |
| 7,476,239 | B2 | 1/2009 | Jackson | |
| 7,618,443 | B2 | 11/2009 | Abdou | |
| 7,635,366 | B2 | 12/2009 | Abdou | |
| 7,662,175 | B2 | 2/2010 | Jackson | |
| 7,666,185 | B2 | 2/2010 | Ryan et al. | |
| 7,682,379 | B2 | 3/2010 | Mathieu et al. | |
| 7,766,915 | B2 | 8/2010 | Jackson | |
| 7,780,706 | B2 | 8/2010 | Marino et al. | |
| 7,794,482 | B2 | 9/2010 | Mathieu et al. | |
| 7,854,752 | B2 | 12/2010 | Colleran et al. | |
| 7,857,836 | B2 | 12/2010 | Huebner et al. | |
| 7,862,591 | B2 | 1/2011 | Dewey et al. | |
| 7,875,065 | B2 | 1/2011 | Jackson | |
| 7,887,569 | B2 | 2/2011 | Frigg | |
| 7,901,437 | B2 | 3/2011 | Jackson | |
| 7,909,852 | B2 | 3/2011 | Boomer et al. | |
| 7,927,359 | B2 | 4/2011 | Trautwein et al. | |
| 7,935,126 | B2 | 5/2011 | Orbay et al. | |
| 7,942,909 | B2 | 5/2011 | Hammill, Sr. et al. | |
| 7,942,910 | B2 | 5/2011 | Doubler et al. | |
| 7,942,911 | B2 | 5/2011 | Doubler et al. | |
| 7,947,065 | B2 | 5/2011 | Hammill, Sr. et al. | |
| 7,951,170 | B2 | 5/2011 | Jackson | |
| 7,951,173 | B2 | 5/2011 | Hammill, Sr. et al. | |
| 7,951,179 | B2 | 5/2011 | Matityahu | |
| 7,967,850 | B2 | 6/2011 | Jackson | |
| 8,012,177 | B2 | 9/2011 | Jackson | |
| 8,025,681 | B2 | 9/2011 | Colleran et al. | |
| 2001/0014807 | A1 | 8/2001 | Wagner et al. | |
| 2001/0021851 | A1 | 9/2001 | Eberlein et al. | |
| 2001/0037112 | A1 | 11/2001 | Brace et al. | |
| 2001/0041894 | A1 | 11/2001 | Campbell et al. | |
| 2001/0047172 | A1 | 11/2001 | Foley et al. | |
| 2001/0047174 | A1 | 11/2001 | Donno et al. | |
| 2002/0013586 | A1 | 1/2002 | Justis et al. | |
| 2002/0016595 | A1 | 2/2002 | Michelson | |
| 2002/0022843 | A1 | 2/2002 | Michelson | |
| 2002/0045896 | A1 | 4/2002 | Michelson | |
| 2002/0045898 | A1 | 4/2002 | Freid et al. | |
| 2002/0045899 | A1 | 4/2002 | Errico et al. | |
| 2002/0049444 | A1 | 4/2002 | Knox | |
| 2002/0058939 | A1 | 5/2002 | Wagner et al. | |
| 2002/0065517 | A1 | 5/2002 | Paul | |
| 2002/0068938 | A1 | 6/2002 | Jackson | |
| 2002/0077630 | A1 | 6/2002 | Lin | |
| 2002/0111630 | A1 | 8/2002 | Ralph et al. | |
| 2002/0120268 | A1 | 8/2002 | Berger | |
| 2002/0120271 | A1 | 8/2002 | Dixon et al. | |
| 2002/0120272 | A1 | 8/2002 | Yuan et al. | |
| 2002/0120273 | A1 | 8/2002 | Needham | |
| 2002/0128654 | A1 | 9/2002 | Steger et al. | |
| 2002/0128655 | A1 | 9/2002 | Michelson | |
| 2002/0151893 | A1 | 10/2002 | Santilli | |
| 2002/0151899 | A1 | 10/2002 | Bailey et al. | |
| 2002/0151900 | A1 | 10/2002 | Glascott | |
| 2002/0156474 | A1 | 10/2002 | Wack et al. | |
| 2002/0161370 | A1 | 10/2002 | Frigg et al. | |

| | | | | | |
|---|---|---|---|---|---|
| 2002/0173790 A1 | 11/2002 | Chang et al. | EP | 0988833 | 3/2000 |
| 2002/0183747 A1 | 12/2002 | Jao et al. | EP | 0995404 | 4/2000 |
| 2002/0183754 A1 | 12/2002 | Michelson | EP | 0 999 796 B1 | 5/2000 |
| 2002/0183755 A1 | 12/2002 | Michelson | EP | 0 767 631 B1 | 12/2000 |
| 2002/0183756 A1 | 12/2002 | Michelson | EP | 1 106 144 A1 | 6/2001 |
| 2002/0183757 A1 | 12/2002 | Michelson | EP | 0683646 | 10/2001 |
| 2002/0188296 A1 | 12/2002 | Michelson | EP | 1169971 | 1/2002 |
| 2003/0018335 A1 | 1/2003 | Michelson | EP | 1 118 5210 | 3/2002 |
| 2003/0023242 A1 | 1/2003 | Harrington, Jr. | EP | 1 220 645 B1 | 7/2002 |
| 2003/0040749 A1 | 2/2003 | Grabowski et al. | EP | 1 306 058 A2 | 7/2002 |
| 2003/0045880 A1 | 3/2003 | Michelson | EP | 1106114 | 2/2003 |
| 2003/0060828 A1 | 3/2003 | Michelson | EP | 1285632 | 2/2003 |
| 2003/0078583 A1 | 4/2003 | Biedermann et al. | EP | 0 874 595 B1 | 3/2003 |
| 2003/0093082 A1 | 5/2003 | Campbell et al. | EP | 0 809 971 B1 | 4/2003 |
| 2003/0105462 A1 | 6/2003 | Haider | EP | 0876128 | 5/2003 |
| 2003/0130661 A1 | 7/2003 | Osman | EP | 1336383 | 8/2003 |
| 2003/0149434 A1 | 8/2003 | Paul | EP | 0828459 | 9/2003 |
| 2003/0153920 A1 | 8/2003 | Ralph et al. | EP | 1340468 | 9/2003 |
| 2003/0181912 A1 | 9/2003 | Michelson | EP | 1346697 | 9/2003 |
| 2003/0187440 A1 | 10/2003 | Richelsoph et al. | EP | 1364623 | 11/2003 |
| 2003/0187441 A1 | 10/2003 | Bolger et al. | EP | 1075226 | 3/2004 |
| 2003/0187442 A1 | 10/2003 | Richelsoph et al. | FR | 2435243 | 4/1980 |
| 2003/0187509 A1 | 10/2003 | Lemole, Jr. | FR | 2519857 | 7/1983 |
| 2003/0191471 A1 | 10/2003 | Michelson | FR | 2556583 | 6/1985 |
| 2003/0191472 A1 | 10/2003 | Michelson | FR | 2740321 | 4/1997 |
| 2003/0208204 A1 | 11/2003 | Bailey et al. | FR | 2794963 | 12/2000 |
| 2003/0225409 A1 | 12/2003 | Freid et al. | FR | 2810532 | 12/2001 |
| 2004/0019353 A1* | 1/2004 | Freid et al. ............ 606/69 | SU | 1424824 | 9/1988 |
| 2004/0030338 A1 | 2/2004 | Paul | WO | 8803781 | 6/1988 |
| 2004/0087951 A1 | 5/2004 | Khalili | WO | WO 88/03781 | 6/1988 |
| 2004/0097934 A1 | 5/2004 | Farris et al. | WO | WO 91/03994 | 4/1991 |
| 2004/0097935 A1 | 5/2004 | Richelsoph et al. | WO | 9417744 | 8/1994 |
| 2004/0097950 A1 | 5/2004 | Foley et al. | WO | WO 95/25474 | 9/1995 |
| 2004/0122426 A1 | 6/2004 | Michelson | WO | WO 95/31941 | 11/1995 |
| 2004/0127896 A1 | 7/2004 | Lombardo et al. | WO | WO 96/00530 | 1/1996 |
| 2004/0127899 A1 | 7/2004 | Konieczynski et al. | WO | 9605778 | 2/1996 |
| 2004/0127900 A1 | 7/2004 | Konieczynski et al. | WO | WO 96/08206 | 3/1996 |
| 2004/0158246 A1 | 8/2004 | Assaker et al. | WO | WO 96/29948 | 10/1996 |
| 2004/0186482 A1 | 9/2004 | Kolb et al. | WO | 9639975 | 12/1996 |
| 2004/0204710 A1 | 10/2004 | Patel et al. | WO | WO 97/22306 | 6/1997 |
| 2004/0204716 A1 | 10/2004 | Fanger et al. | WO | 9834553 | 8/1998 |
| 2004/0204717 A1 | 10/2004 | Fanger et al. | WO | 9834556 | 8/1998 |
| 2004/0220570 A1 | 11/2004 | Frigg | WO | 9851226 | 11/1998 |
| 2004/0220571 A1 | 11/2004 | Assaker et al. | WO | WO 99/04718 | 2/1999 |
| 2005/0038436 A1 | 2/2005 | Michelson | WO | 9921502 | 5/1999 |
| 2005/0049593 A1 | 3/2005 | Duong et al. | WO | WO 99/56653 | 11/1999 |
| 2005/0192577 A1 | 9/2005 | Mosca et al. | WO | WO 9959492 | 11/1999 |
| 2005/0234456 A1 | 10/2005 | Malandain | WO | 0003653 | 1/2000 |
| 2006/0122602 A1 | 6/2006 | Konieczynski et al. | WO | WO 00/25689 | 5/2000 |
| 2006/0122604 A1 | 6/2006 | Gorhan et al. | WO | 0066011 | 11/2000 |
| 2006/0149256 A1 | 7/2006 | Wagner et al. | WO | WO 00/78238 | 12/2000 |
| 2006/0161157 A1 | 7/2006 | Mosca et al. | WO | 0101874 | 1/2001 |
| 2006/0200147 A1 | 9/2006 | Ensign et al. | WO | 0126566 | 4/2001 |
| 2006/0217725 A1 | 9/2006 | Suh | WO | WO 01/26567 | 4/2001 |
| 2006/0235399 A1 | 10/2006 | Carls et al. | WO | 0149191 | 7/2001 |
| 2006/0241616 A1 | 10/2006 | Konieczynski et al. | WO | 0164144 | 9/2001 |
| 2007/0010817 A1 | 1/2007 | de Connick | WO | WO 01/82804 | 11/2001 |
| 2007/0162016 A1 | 7/2007 | Matityahu | WO | WO 01/82805 | 11/2001 |
| 2011/0112584 A1 | 5/2011 | Frigg | WO | WO 01/89400 | 11/2001 |
| | | | WO | WO 01/89428 | 11/2001 |
| FOREIGN PATENT DOCUMENTS | | | WO | 02076317 | 10/2002 |
| | | | WO | 02080789 | 10/2002 |
| DE | 1949923 | 4/1971 | WO | 02098276 | 12/2002 |
| DE | 2933141 | 4/1980 | WO | WO 02/098277 | 12/2002 |
| DE | 4409833 | 10/1995 | WO | 03007826 | 1/2003 |
| DE | 19548395 | 9/1997 | WO | 03017856 | 3/2003 |
| EP | 0 179695 A1 | 4/1986 | WO | 03053262 | 7/2003 |
| EP | 0 201 024 B1 | 11/1986 | WO | 03063714 | 8/2003 |
| EP | 0 242 842 B1 | 10/1987 | WO | WO 03/071966 | 9/2003 |
| EP | 0 251 583 A2 | 1/1988 | | | |
| EP | 0 410 309 A1 | 1/1991 | OTHER PUBLICATIONS | | |
| EP | 0 455255 A1 | 11/1991 | | | |
| EP | 0 471418 A1 | 2/1992 | | | |
| EP | 0502815 | 9/1992 | | | |
| EP | 0599640 | 6/1994 | | | |
| EP | 0 699 057 B1 | 3/1996 | | | |
| EP | 0 809 972 A3 | 12/1997 | | | |
| EP | 0 897 697 A1 | 2/1999 | | | |
| EP | 0 903 113 A2 | 3/1999 | | | |
| EP | 0984728 | 3/2000 | | | |

Omeis et al., "History of Instrumentation for Stabilization of the Subaxial Cervical Spine", Neurosurg Focus 16 (1): Article 10, 2004.

Chang, J.H.; Chang, G.L.; Hsu, A.T.. Kinematic Study of Cervical Vertebrae Adjacent to Fixation Procedures. 1999 Bioengineering Conference, Big Sky, Montana, USA. Jun. 1999. 2 pages.

Tippets, Richard H., MD; Apfelbaum, Ronald I., MD. Anterior Cervical Fusion with the Caspar Instrumentation System.

*Neurosurgery*, vol. 22, No. 6, Part 1. Jun. 1998. 6 pages. Lippincott Williams & Wilkins; Hagerstown, MD, USA.

Benzel, Edward, MD; Leon, Steven, MD. Enhancing Cervical Spine Fusion, www.medscape.com. Mar. 2001. 31 pages.

Paramour, Christoper, MD; Dickman, Curtis, MD; Sonntag, Volker, MD. Radiographic and Clinical Follow-Up Review of Caspar Plates in 49 Patents. *Journal of Neurosurgery*, vol. 84, No. 6. Jun. 1996. 5 pages. American Association of Neurological Surgeons; Rolling Meadows, IL, USA.

Clausen, John; Tyken, Timothy, MD; Traynelis, Vincent, MD; Sawin, Paul, MD; Dexter, Franklin, MD; Goel, Vijay. Biomechanical Evaluation of Caspar and Cervical Spine Locking Plate Systems in a Cadaveric Model. *Journal of Neurosurgery*, vol. 84, No. 6. Jun. 1996. 9 pages. American Association of Neurological Surgeons; Rolling Meadows, IL, USA.

Bose, Bikash, MD. Anterior Cervical Fusion Using Caspar Plating: Analysis of Results and Review of the Literature. *Surgical Neurology*, vol. 29, No. 1. Jan. 1998. 8 pages. Elsevier Biomedical; New York, NY, USA.

Pitzen, T.; Steudel, W.; Oxland, T. The Effect of Posterior Element Injury on Cervical Spine Flexibility While Using Anterior Plates With and Without Posterior Fixation. An In Vitro Trauma Model. $52^{nd}$ Annual Meeting of the German Society of Neurosurgery, Bielefeld, Germany. May 2001. 1 page.

Caspar, W; Barbier, DD; Klara, PM. Anterior Cervical Fusion and Caspar Plate Stabilization for Cervical Trauma. *Neurosurgery*, vol. 25, No. 4. Oct. 1989. Lippincott Williams & Wilkins; Hagerstown, MD, USA. 1 page.

Armstrong, Gordon; Chow, Donald. The Contoured Anterior Spinal Plate. *Spinal Instrumentation*. 1992. Williams & Wilkins; Baltimore, MD, USA.

Zdeblick, Thomas, MD; Ghanayem, Alexander, MD; Rapoff, Andrew, MS; Swain, Carol, MS; Bassett, Tim, MD; Cooke, Mary, MS; Markel, Mark, DVM. Cervical Interbody Fusion Cages: An Animal Model With and Without Bone Morphogenetic Protein. *Spine*, vol. 23, No. 7. Apr. 1998. Lippincott Williams & Wilkins; Hagerstown, MD, USA. 8 pages.

Takahashi, Toshiyuki; Tominaga, Teiji; Yoshimoto, Takashi; Koshu, Keiji; Tokobori, A. Toshimitsu; Aizawa, Yoichi. Biomechanical Evaluation of Hydroxyapatite Intervertebral Graft and Anterior Cervical Plating in a Porcine Cadaveric Model. *Bio-medical Materials and Engineering*, vol. 7, No. 2. 1997. IOS Press; Amsterdam, Netherlands. 7 pages.

Chen, Ing-Ho; Yang, Rong-Sen; Chen, Po-Quang. Plate Fixation for Anterior Cervical Interbody Fusion. *Journal of the Formosan Medical Association*, vol. 90, No. 2. Feb. 1991. Scientific Communications International; Hong Kong, China. 4 pages.

International Search Report of the International Searching Authority dated Dec. 22, 2004, from related International (PCT) Application No. PCT/US04/03205, 4 pages.

Written Opinion of the International Searching Authority dated Nov. 29, 2004, from related International (PCT) Application No. PCT/US04/03205, 4 pages.

* cited by examiner

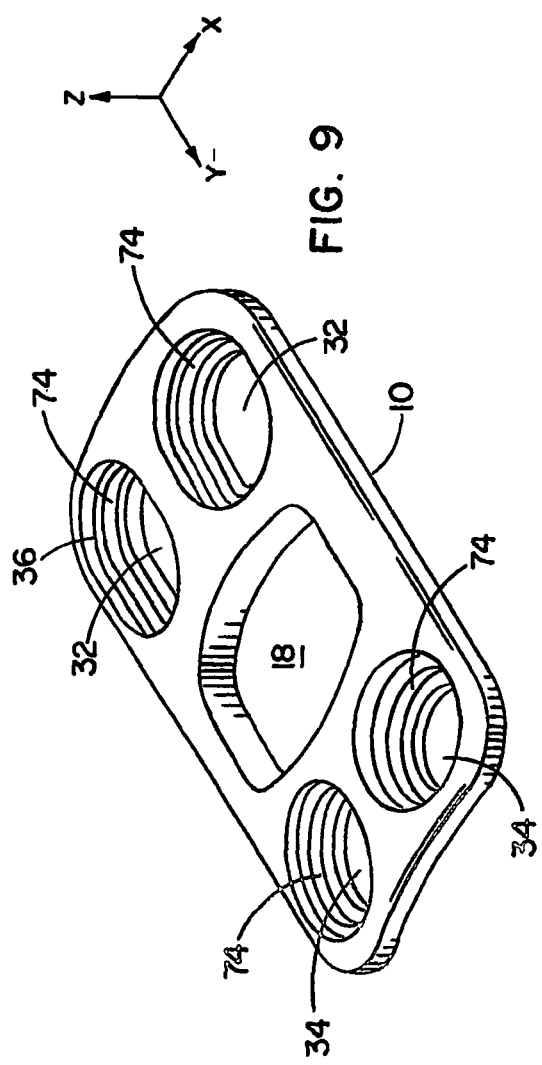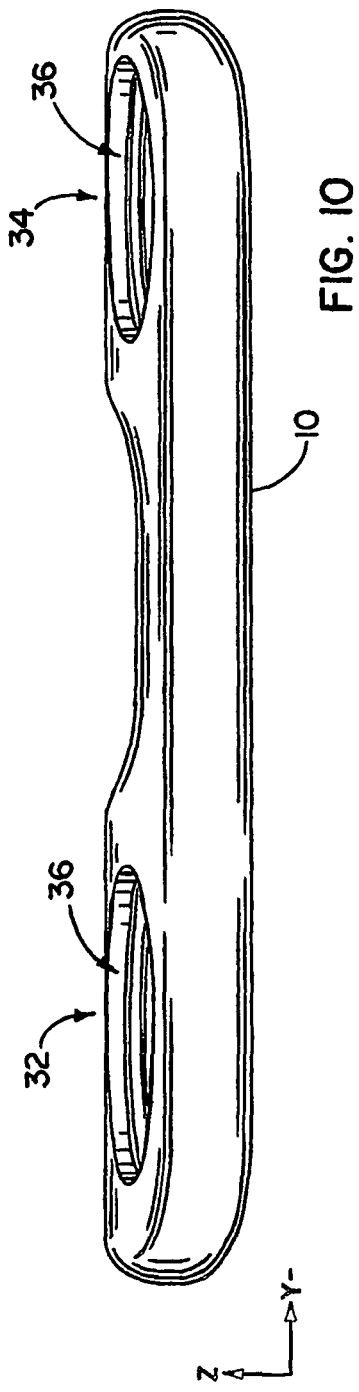

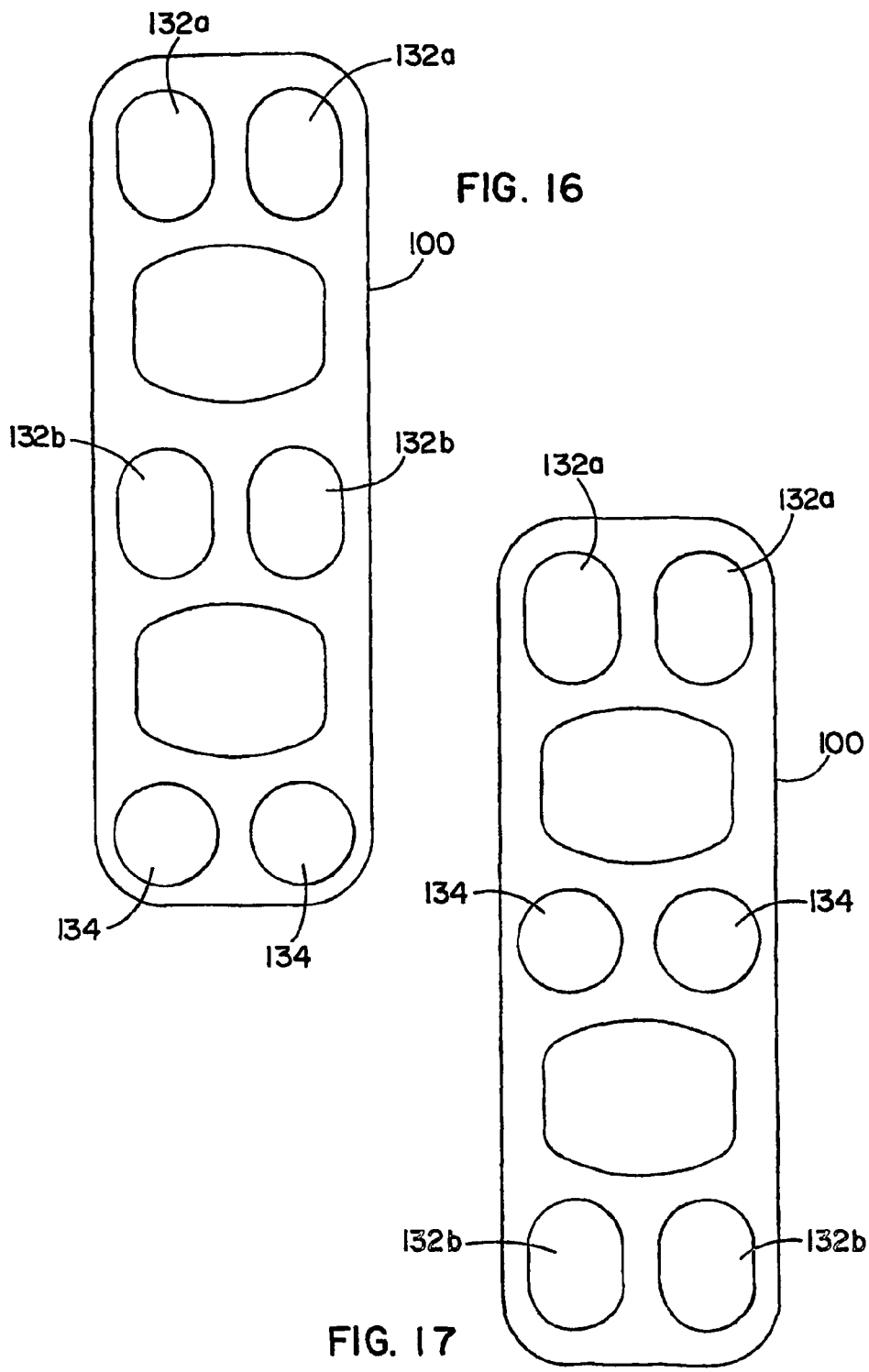

BONE PLATE SYSTEM

CROSS-REFERENCE TO RELATED APPLICATIONS

This application claims priority to United States Provisional Application Ser. No. 60/445,005, filed Feb. 5, 2003, and entitled "Bone Plate System,"

FIELD OF THE INVENTION

The invention relates to systems for securing bones and, in particular, to a bone plate system, for securing bones to aid in fusion of bones.

BACKGROUND OF THE INVENTION

A number of procedures and systems are used currently for securing bones. One example is the use of a bone plate being secured to a plurality of bones to prevent generally the relative movement of the bones enabling the bones to fuse or heal. Bone plate systems are placed across the joint or fracture site of bones or site of desired bone fusion. As used herein, the term "bone" is used to designate a bone in its entirety, such as a spinal vertebra, as well as a bone fragment.

A number of considerations are involved in the design and use of bone plate systems. For instance, bone plates are implanted in a living tissue environment during a surgical procedure. It is important that no portion of unsecured, foreign material, such as a component of the bone plate system, may be left in the tissue environment post-procedure. Often being relatively small and including component parts, many current bone plates systems are problematic because they cannot be simply handled or manipulated by a surgeon or technician, and because their small components may be dropped into the open-tissue environment and must then be retrieved.

Current bone plates are difficult to place in the desired location because they do not enable the surgeon the ability to simultaneously view the fusion site with the plate in position before securing the plate. This shortcoming is compounded because the tissue environment is difficult to view and presents limiting access to the seam or fusion site.

In many bone plate system applications, it is relatively difficult to secure tightly the bones relative to one another for fusion. As an example, when spinal vertebrae are secured for fusion, bone graft is placed between the vertebral sections. A bone plate is then secured with screws across the fusion site to secure the vertebrae along the spinal axis. It can be difficult to compress properly the vertebral sections because the surgical procedure is performed while the patient is lying prone under anesthesia. However, such a spinal procedure would benefit from the compressive force of gravity. That is, when the patient is allowed to stand erect, gravity is able to compress the vertebral sections and the graft material to benefit healing. In order to enable this, however, the bone plate must allow a slight compression of, or shortening of the distance between, the securing screws in the direction along the spinal axis.

A problem occasionally encountered in the use of bone plate systems is "backing out" of the screws. Specifically, the bone plate is secured with a plurality of screws driven into bones. Due to stresses upon the bones, the performance of some simple bone plate systems has suffered from the screws loosening from, or backing out of, the bones. The loosening of the screws may result from the screw rotating counterclockwise so as to unthread itself from the bone, or from the threads created in the bone being stripped or otherwise allowing the screw to recede from the bone. Loosening of the screws from the bone allows the plate to move and undermines the ability of the plate to aid in bone fusion, and may cause injury to surrounding tissues.

Another consideration is that the screws and plates are located commonly in a particular orientation by the surgeon implanting the system. For instance, the central axis of the screw can have a particular angle relative to the plate. A surgeon bases this angle on a number of factors to which the performance of the system owes itself. When one or more screws is permitted to alter its desired orientation relative to the plate, the bones tend not to be sufficiently secured relative to each other to optimize the performance of the bone plate system.

Therefore, it is desirable to have an improved bone plate system that, among other things, addresses the foregoing considerations and shortcomings.

BRIEF DESCRIPTION OF THE DRAWINGS

FIG. 9 is a perspective view of a bone plate of the bone plate system of FIG. 1;

FIG. 10 is a side elevation view of the bone plate of FIG. 9;

FIG. 16 is a plan view of another embodiment of a bone plate including features of the present invention;

FIG. 17 is a plan view of another embodiment of a bone plate including features of the present invention;

DETAILED DESCRIPTION OF THE PREFERRED EMBODIMENT(S)

Figure 1:
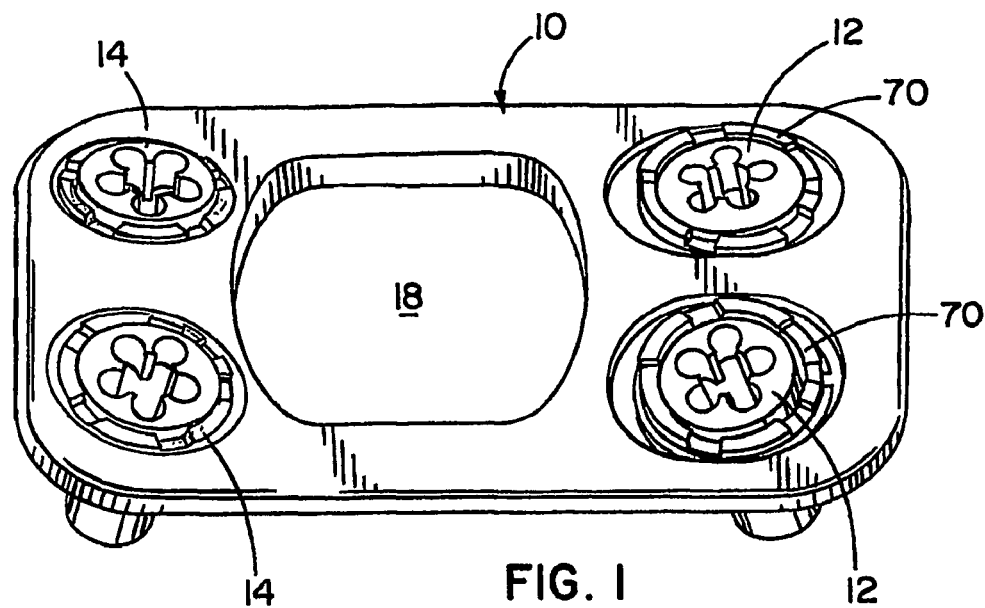
FIG. 1 is a perspective view of a bone plate system including features in accordance with the present invention.
Figure 2:
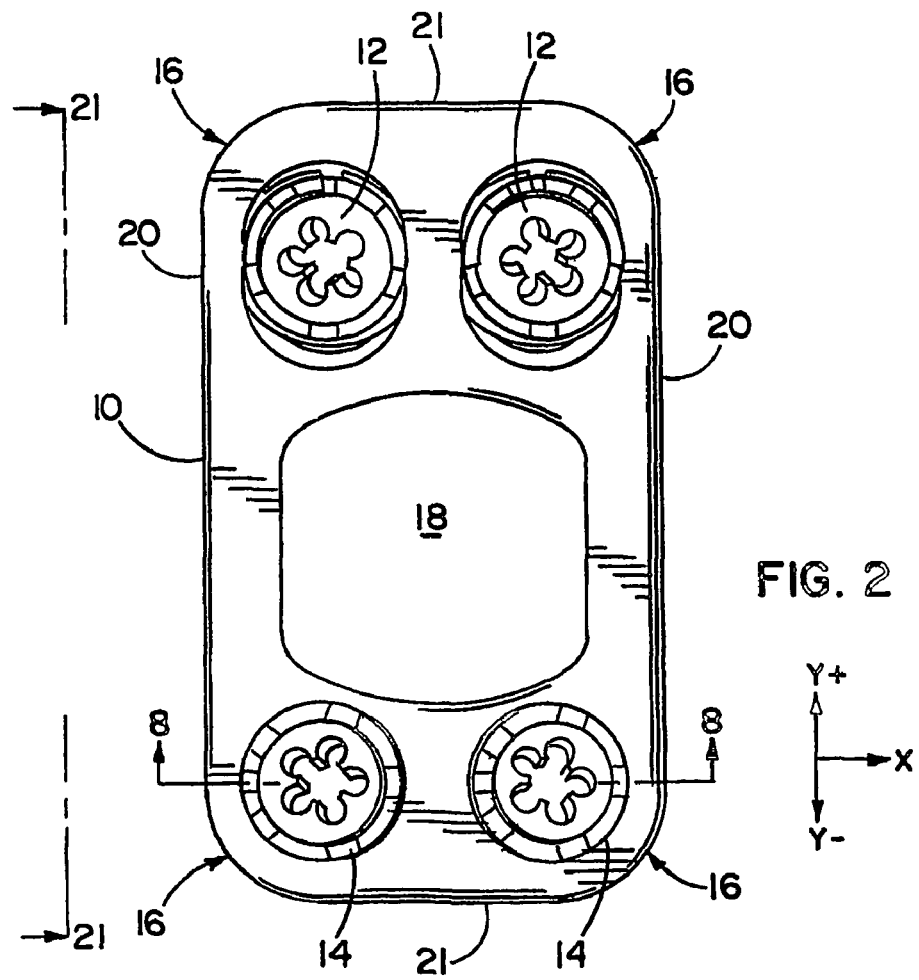
FIG. 2 is plan elevation view of the bone plate system of FIG. 1.

Referring initially to FIGS. 1 and 2, there is illustrated an exemplary bone plate system including features in accordance with the present invention. The illustrated bone plate system includes a bone plate 10 with a window and a plurality of screw holes 32, 34, a plurality of bone screws 12, 14 and corresponding screw locks 70. The bone plate 10 extends between two bones or fragmented bone segments to aid in fusion of such. The window 18 aids placement of the bone plate 10 during the implant procedures. The screws 12, 14 secure the bone plate to the bone(s), and the screw locks 70 lock the heads of the screws 12, 14 to prevent unintentional backing out of the screws 12, 14. One set of screw holes 32 can be elongated to enable the vertebrae to shift, such as when caused by gravity when the patient is upright. This shifting is referred to herein as dynamization.

Figure 4:
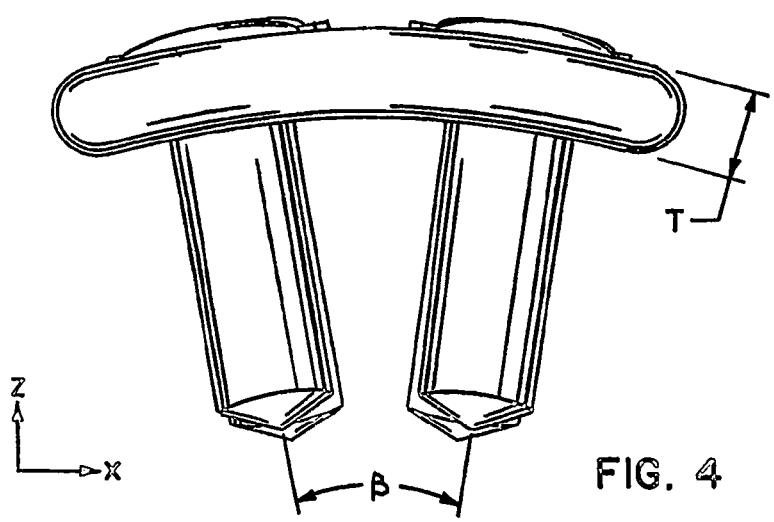
FIG. 4 is an end elevational view of the bone plate system of FIG. 1.
Figure 5:
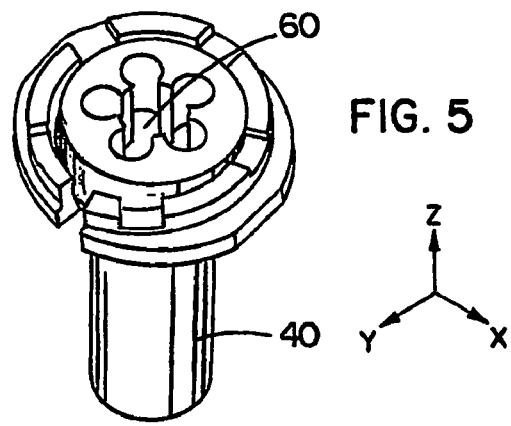
FIG. 5 is a perspective view of a screw and screw lock collar of the bone plate system of FIG. 1.

More specifically, the bone plate 10 is depicted with a generally rectangular plate-like configuration. As can be seen in FIG. 4, the plate 10 preferably has an arched profile about its longitudinal axis 11. The arched profile allows the plate 10 to secure to the contours of the vertebrae.

Bone anchors, such as bone screws 12, 14, secure the plate 10 to bones or vertebrae. The arch of the plate 10 provides the screws 12, 14 with an included angle β relative to one another for securing to the vertebrae. The screws 12, 14 also are preferably polyaxial relative to the plate, and the plate 10 is configured to provide such relative disposition. The arched profile of the plate 10 assists to orient the screws 12, 14, though the actual included angle β when the screws 12, 14 are secured may significantly differ from the radius of curvature of the plate 10 due to the polyaxial capability. The plate 10 may have a uniform thickness, or alternatively, it may have a cross-sectional thickness that varies, specifically being thinner in the region of screw holes 12, 14 provided for the screws 12, 14, and therebetween, and thicker in the region of the plate 10 periphery. In general, thickness of the plate preferably is to be no greater than approximately 3 to 5 millimeters.

The plate 10 may have rounded corners 16 to reduce risk of scarring or other complications due to contact between the plate 10 and soft tissues, such as skin and fat and muscles, particularly contact caused by movement of the person. For these same reasons, the side edges 20 and the longitudinal edges 21 of the plate 10 are rounded, as well.

As is known, in a bone graft for spinal fusion, a spinal disc is removed from between vertebrae, and graft material is inserted between the vertebrae. The plate 10 is used to secure the adjacent vertebrae and hold the graft material in place so that the vertebrae and graft material fuse, or in the absence of graft material, the vertebrae or other bones fuse. Alternatively, a fractured or broken vertebra may be secured across the fracture or break. In securing the vertebral sections, the surgeon preferably can view the site of fusion while positioning the plate 10 over the fusion site during the implant procedure. Accordingly, the plate 10 is provided with the generally rectangular window 18. In an alternative embodiment, the window 18 may have a different configuration, such as a circle or oval. As an additional alternative, the plate 10 may be constructed as having a central portion with lateral cut-out portions (not shown) so that the fusion site or seam can be seen to the lateral sides (X direction). The interior edges of the window 18 are rounded for the same safety reasons discussed above regarding the side and longitudinal edges 20, 21 of the plate 10.

Figure 3:
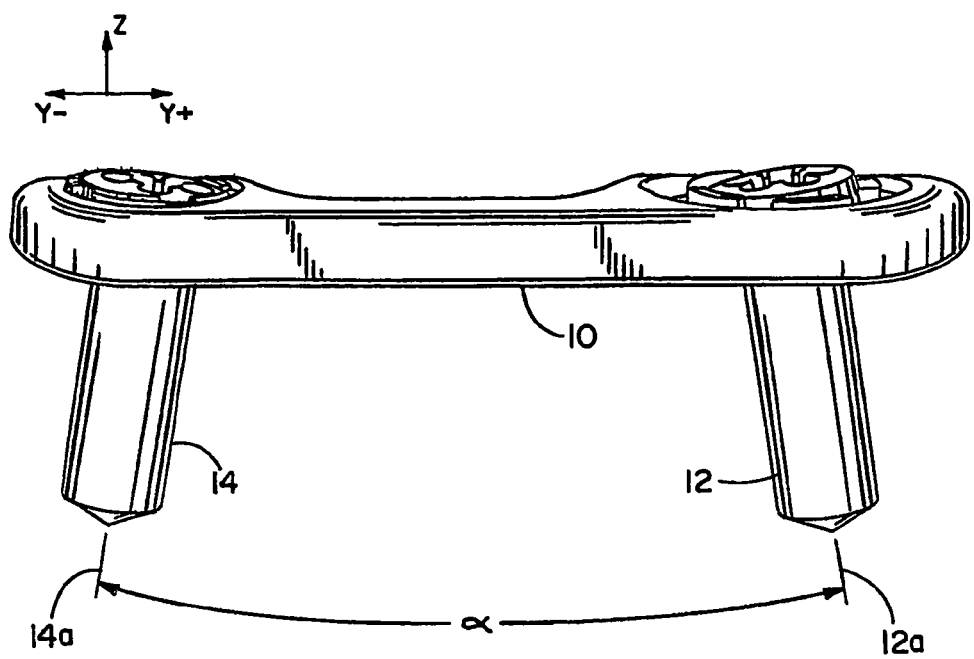
FIG. 3 is a side elevation view of the bone plate system of FIG. 1.

Preferably, the screws 12, 14 are bone screws mounted anteriorly or laterally in the vertebrae. The bores 32, 34 are sized and shaped to allow the screws 12, 14 polyaxial movement so that they can be oriented relative to the plate as dictated by the structure of the vertebrae to effectively secure into such vertebrae, or in the orientation preferred or deemed proper by the surgeon. As illustrated, FIG. 3, for example, depicts the screws 12, 14 at an orientation relative to the bone plate 10 defined by an included angle .alpha. between the respective longitudinal axes 12a and 14a of the screws 12, 14.

As illustrated in FIGS. 8-13, the bone plate 10 includes bores 32,34 or holes through which the screws 12, 14 are inserted and extend therethrough. As can be seen, the bores 32, 34 are socket-configured and form a recess 36 opening through the top 35 of the plate 10. The recess 36 enables the head 50 of each screw 12, 14, and any associated screw lock (such as collar 70, see below), to be counter-sunk in their respective bore 32, 34 so that they do not protrude out from the bores 32, 34 beyond the top of the plate 10 when properly implanted and secured to a bone structure.

In a first set of bores 32, each has an elongated shape with a major axis in the Y direction and a minor axis in the X direction, with reference to the illustrated coordinate system. Preferably, the bores of the first set 32 generally have two straight side segments of congruent length and parallel to the Y direction, which are joined by arcuate transitional segments at the ends. Alternatively, the upper bores 32 may have straight segments parallel to the X direction of the ends of the bores 32 to join the straight sides parallel to the Y direction. As a further alternative, the bores 32 may have a generally oval perimeter shape.

When the plate 10 is secured to bone structure, the shape of the bores 32 permit the plate 10 and corresponding screws 12 to adjust slightly along the major axis relative to the plate 10. For example, when a person fitted with the plate 10 at the spine stands erect, the person's weight (the force of gravity) and normal movement of the body commonly compress the vertebral sections to which the screws 12 and 14 are fastened. To utilize this compressive force for improvement of bone fusion, the screws 12 and bone plate 10 are allowed to adjust relative to one another at the bores of the first set in the vertical direction relative to the person. This adjustability is referred to as dynamization, and the screws are referred to as dynamized screw settings or anchors. The screws 32 closely match and fit the bores 32 along the minor axis to prevent or minimize any lateral motion of the plate 10 or bones relative to one another.

The opposing set of screws 14 are secured in the second set of bores 34. In the present embodiment, each bore 34 of the second set has a generally circular perimeter shape so that the screws 14 closely match and fit in the bores 34 in a manner that prevents or minimizes motion of the plate 10 relative to the bone structure into which screws 14 are secured. In an alternative embodiment, the screws 14 and bores 34 may also be dynamized.

The number, combination and position of dynamized and non-dynamized bores is not limited by the present invention. For instance, as illustrated in FIG. 16, a plate 100 is depicted with a pair of adjacent dynamized bores 132a for a first bone section, a pair of adjacent dynamized bores 132b for a second bone section, and a pair of non-dynamized bores 134 for a third bone section. As an example of the use of plate 100, three (or more) vertebrae may be secured in a larger spinal fusion procedure, the results of which would benefit from gravitational compression as discussed. Accordingly, dynamized screws and bores 132a, 132b, 134 may be secured to a plurality of vertically aligned bones such that each of the bones and its attendant screw may adjust towards the other bones. By way of another example, as illustrated in FIG. 17, the non-dynamized holes can be situated between the dynamized holes. Furthermore, all of the holes can be dynamized or non-dynamized. Other configurations are contemplated and within the scope of embodiments of the present invention.

Figure 8:
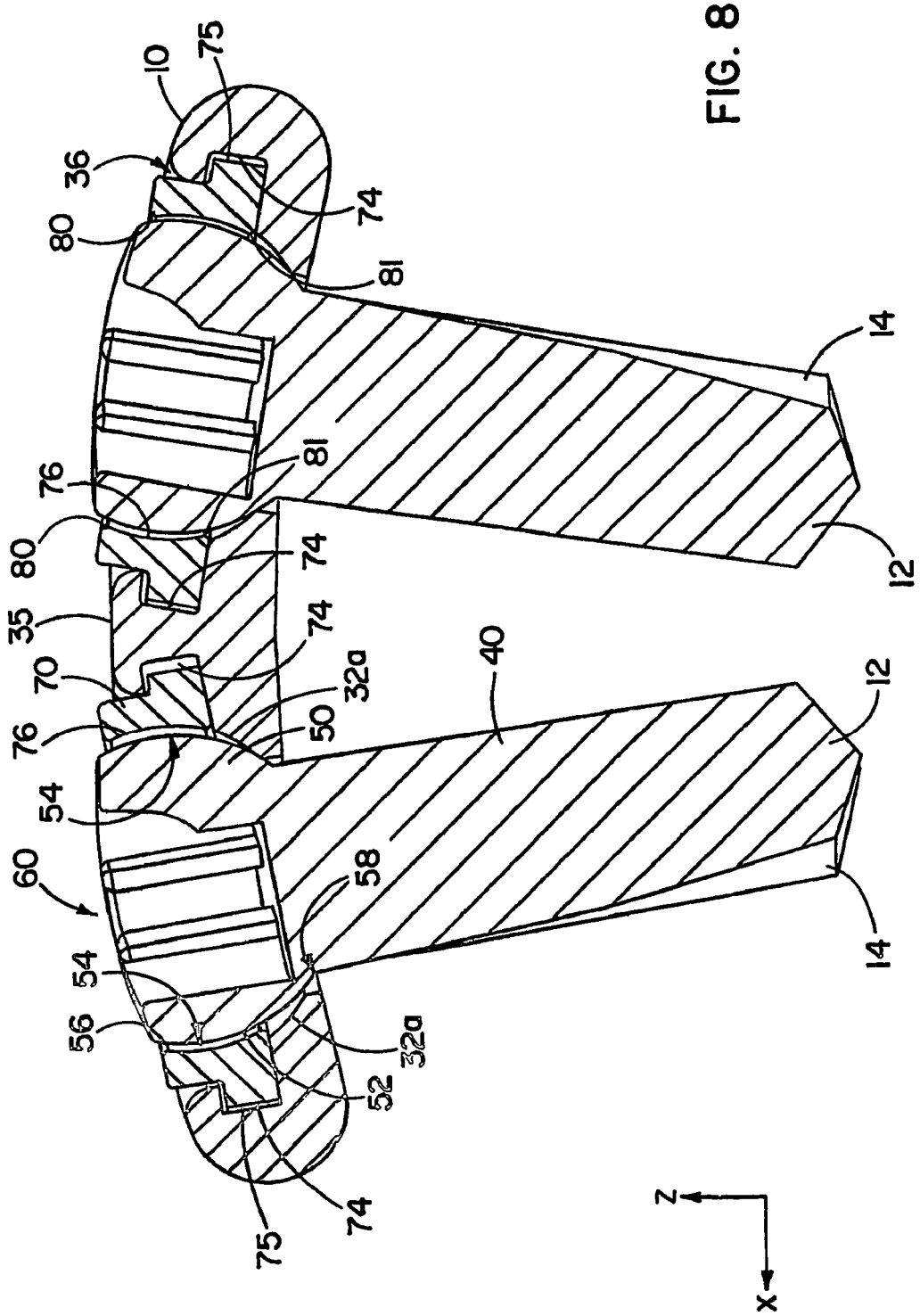
FIG. 8 is an end cross-sectional view of the bone plate system taken along line 8-8 of FIG. 2 with the screw lock collar in the unlocked state.

As illustrated in FIG. 8, the screws 12, 14 are generally identical, and each includes a shank portion 40 and a head 50.

The shank portion 40 is generally threaded, such as with a bone screw thread, so that it can be secured into a bone structure when the screw 12, 14 is turned into the bone structure. The profile of the shank portion 40 may have a variety of configurations, as is known in the art, may be self-tapping, may be self-drilling, and may be inserted into a pre-tapped hole in the bone.

In the illustrated embodiment of FIG. 8, the head 50 has a partially spherical configuration at its outer side surface 52. The greatest diametral portion 54 of the head 50 is located between the top-most point 56 and the bottom-most point 58 of the head 50. The center of the head 50 defines a recessed structure 60 for mating with a driving tool (not shown) for driving the screws 12, 14 into the bones.

Each screw 12, 14 is preferably coupled with a screw lock such as collar 70, in the present embodiment. The screw lock 70 locks the screws 12, 14 into place with the bone plate 10 in order to prevent backing-out (either by rotation or thread stripping) of the screws 12, 14 and to secure the screws in their desired orientation relative to the plate 10.

Figure 6:
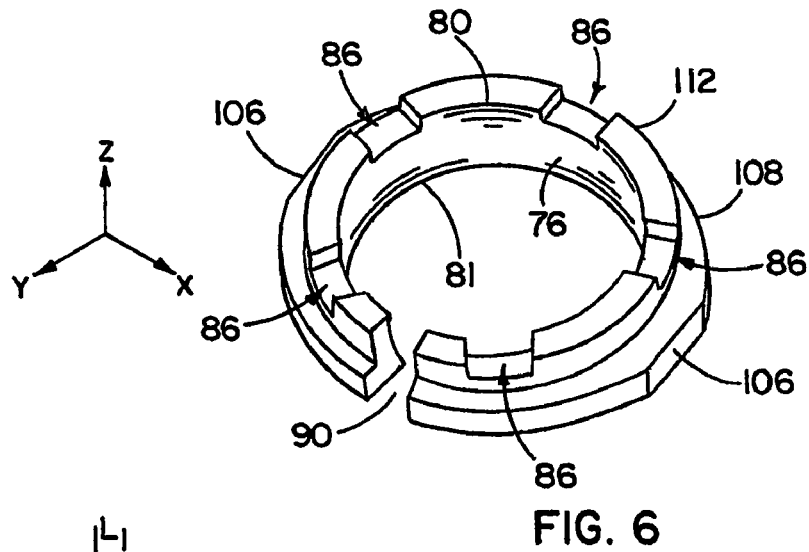
FIG. 6 is a perspective view of the screw lock collar of FIG. 5.
Figure 7:
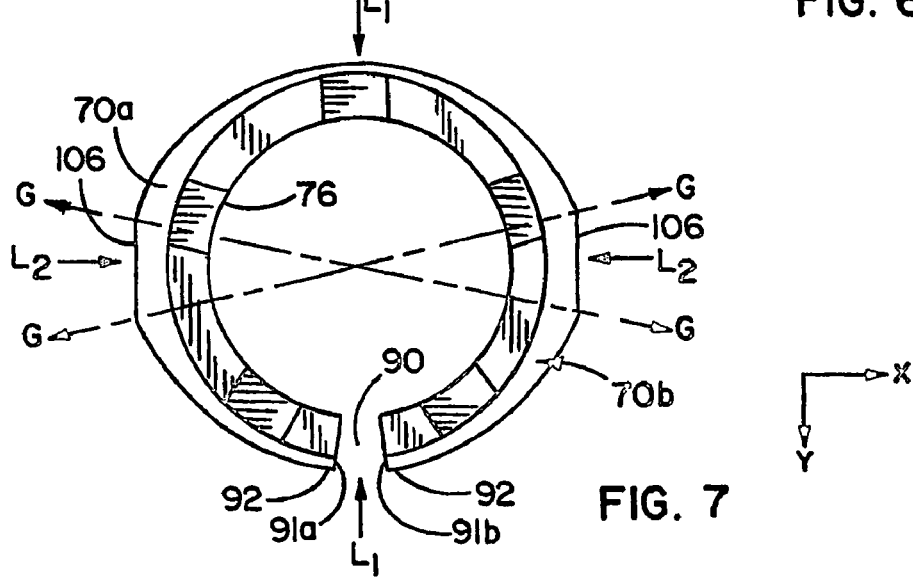
FIG. 7 is a plan view of the screw lock collar of FIG. 5.

In the illustrated embodiment, the screw locks are collars 70 set into channels 74 (see FIGS. 8 and 9). As illustrated in FIGS. 6 and 7, the collars 70 are preferably C-ring collars with an inner surface 76. The collars 70 are substantially located within the recess 36, as illustrated in FIG. 8. The screw locks may be pre-set or pre-inserted so that, in the operating environment, the surgeon need only handle the plate 10 and the included screw locks as a single pre-assembled item. The inner surface 76 is preferably shaped to conform to the above-described partially spherical outer profile of the head 50 of the screws 12, 14. This enables the inner surface 76 to tightly engage and clamp against the outer surface 52 of the head 50 of the screw for locking the screw. This maximizes the contacting surface area between the collar 70 and screw heads 50 to enhance friction therebetween for rotation resistance. This also minimizes potential damage to the collar 70 and head 50 which could result in a less secure lock between the collar 70 and the head 50 and minimizes potential for shearing of pieces of the plate system that would contaminate the tissue environment.

As illustrated in FIG. 8, at least a portion of the partially spherical outer surface 52 engages the collar 70 and a lower portion of the bores 32, 34 of the plate 10. It is preferred that any portions of the plate 10 and collar 70 which contact the screw 12, 14 be closely mated to form a generally continuous contoured contact surface corresponding to the partially spherical outer surface 52. For example, as illustrated, the partially spherical surface 52 of the screw head 50 is contoured to generally correspond to the inner contour 32a of the bore 32 and the inner contour or surface 76 of the collar 70, when in a locked position. The same corresponding surface engagement is preferably with screws 14 and bore 34 and its locking collar 70, as well. However, it should be appreciated that, the head 50 and corresponding collar 70 of a screw set for dynamization, such as screw 12, does not necessarily have a full circumference of contact with the bore 32 as the major axis direction of the bore 32 provides for relative movement therealong. However, where there is contact between the bore 32 and the screw 12 and locking collar 70, a generally close mating of the contours is preferred, including when the screw 12 has been displaced to and is abutting the lower-most portion of the bore 32.

Alternatively, the bores 32, 34 of the plate 10 may be shaped such that the head 50 abuts only the collar 70. For instance, the collar 70 may extend the axial length of head 50, may extend the axial length of the interior of the bores 32, 34, and/or may simply be utilized such that a gap (not represented) exists between the head 50 and the plate 10.

With reference to FIGS. 6 and 8, the inner surface 76 of the collar 70 has an arcuate profile for mating with the partially spherical outer profile of the head 50 of the screws 12, 14. In its natural state, the inner surface 76 has a top lip or edge 80 and a bottom lip or edge 81 where the inner diameter of the collar 70 at the both the top edge 80 and bottom edge 81 is smaller than the largest diametral annular portion 54 of the head 50. As the screw 12, 14 is driven into the bone, the outer surface of the head 50 forces the C-ring collar 70 to expand to permit ingress of the head 50, particularly the largest diametral portion 54 of the head 50, into the collar 70 by forcing against the top edge 80. Once the annular portion 54 of the head 50 passes into the annular plane of the collar 70, the collar 70 then elastically contracts. This provides a "snap-in" like property to the screws 12, 14 and collars 70. In order to prevent the head 50 of the screws 12, 14 in the collar 70 from forcing open the collar 70 at the bottom edge 81, a recess cup 83 is provided for each bore 32, 34 and correspondingly shaped to the bore 32, 34 such that the recess cup 83 interferes with continued translation of the screws 12, 14 through the bores. Alternatively, the collar 70 may permit the screw head 50 to be inserted therein without expanding.

During procedures, a surgeon would align the plate 10, including pre-set collars 70, using the window 18 with the fusion site. Screws 12, 14 would be turned into the bone structure using a proper technique, which includes, for instance, using a pilot hole, a pre-tapped hole, or self-tapping bone screw. As the screws 12, 14 are seated in the collars 70, the collars 70 can be held against rotation as the screw head portion 54 passes through edge 80 of the collar 70 causing the collar 70 to expand to permit the head 50 to seat within the collar 70. The surgeon continues to turn one of the screws 12, 14 until the screw is generally seated. Then, the surgeon turns the collars 70 to lock the screws and specifically the heads thereof in the bores 32, 34 of the plate 10.

It should be noted that, during driving of the screws 12, 14, the friction of the screw 12, 14 against the collar 70 may provide a rotational force to the collar 70. It is preferred that the collar 70 is permitted to rotate only slightly, and more preferably, it is generally not permitted to rotate unless locked by the surgeon. In some cases, it may be necessary to utilize a tool to restrain the movement of the collar 70 until an appropriate time for locking the collars 70. Alternatively, the collar 70 may be restrained from rotating until the screw 12, 14 is nearly seated, at which point the final turning of the screw 12, 14 also rotates and locks the collar 70.

A tool for controlling the rotational movement of the collar 70 is preferably provided as part of the bone plate system. A simple tool (not shown) could be utilized for controlling this movement. The tool would, in the present environment, be designed to mate with notches 86 (see FIG. 6) in the collar 70. The tool and collar 70 would be made of sufficient material and with hardness properties so as not to be susceptible of breaking or losing pieces due to forces being applied so that no foreign matter would be dispensed into the tissue environment. Alternatively, other configurations could be utilized for mating the tool to the collar 70. The collars 70 are locked, as described herein, by rotating the collar 70 once the screws 12, 14 have been set to a sufficient torque in the bone and to secure the plate 10. The friction generated between the collar 70, the screws 12, 14, and the plate 10 should not cause any portion of any these to shear away and become debris in the tissue environment.

As an alternative, the tool (not shown) may include features to combine driving the screws 12, 14 and controlling and locking the collar 70. More specifically, for instance, the tool may have a central driving portion for mating with the head 50 of the screws 12, 14 and have an outer sheath for mating with the collar 70. As the central portion is rotated, the outer sheath may be held in place to restrain the collar 70 against rotation. Once the central portion has driven the screw 12, 14 , to its desired torque, the outer sheath may be rotated to turn and lock the collar 70. The outer sheath may include a handle or grip for controlling its operation.

As alternative, the screws 12, 14 may have the screw lock, such as the collar 70, pre-set or attached to the screw 12, 14 (as opposed to pre-set in the plate 10). As described above, the inner surface 76 of the collar 70 has upper and lower edges 80, 81 smaller in diameter than the largest diametral annular portion 54 of the head, and the screw 12, 14 is mated accordingly within the collar 70. For this alternative, a surgeon may position the plate 10 in the desired position, and turn the screws 12, 14, including the collar 70, into the bones. As the collar 70 reaches the plate 10, the collar 70 may simply move into the top portion of the bore 32, 34 or be compressed in the radial direction in order to fit within the bore 32, 34. Once the collar 70 reaches the channel 74, the collar 70 should expand to fit in the channel 74 and be secure against unintentional axial movement. The inner diameter of the bore 32, 34 in the annular area immediately above the channel 74 in the axial direction may have a larger diameter than the diameter in the annular area immediately below the channel 74 so that the collar 70 being inserted does not pass by the channel 74. In any event, the annular lip surrounding the entrance into the bores can be rounded or tapered to assist in the insertion of the collar into the bores.

As illustrated, the preferred collar 70 has a C-ring configuration with a gap 90 between opposing ends 91a and 91b of arcuate arm portions 70a and 70b of the collar 70. The spaced ends are such that in the locked position they are moved toward each other and the arm portions are clamped tightly against the screw head, whereas in the unlocked position the c-collar is allowed to shift back toward its relaxed configuration with the arm ends moving apart. The outermost edges 92 adjacent the gap 90 preferably are configured so as to minimize hang-ups or digging into the plate 10 when rotated. In one embodiment, the edges 92 may be of slightly reduced diameter as by being beveled or rounded inwardly to prevent contact with the plate 10.

The preferred collar 70 has an annular step construction with a lower step portion 108 with an outer diameter that is greater than an outer diameter of an upper step portion 112. The step portions 108 and 112 have continuous inner diametral surfaces that are flush with each other at the collar to form the inner surface 76 that mates with the head 50 of the screw. This allows the step portion 108 of each collar to seat within the channel 74 and also permits enhancement of the area of the inner arcuate surface 76 which abuts the head 50 of the inserted screws 12, 14 for constraining and securing the screw 12, 14. It also provides the collar 70 with sufficient axial length so that the above-described top portion 80 extends above the greatest diametral portion 54 of the screw head 50.

Figure 18:
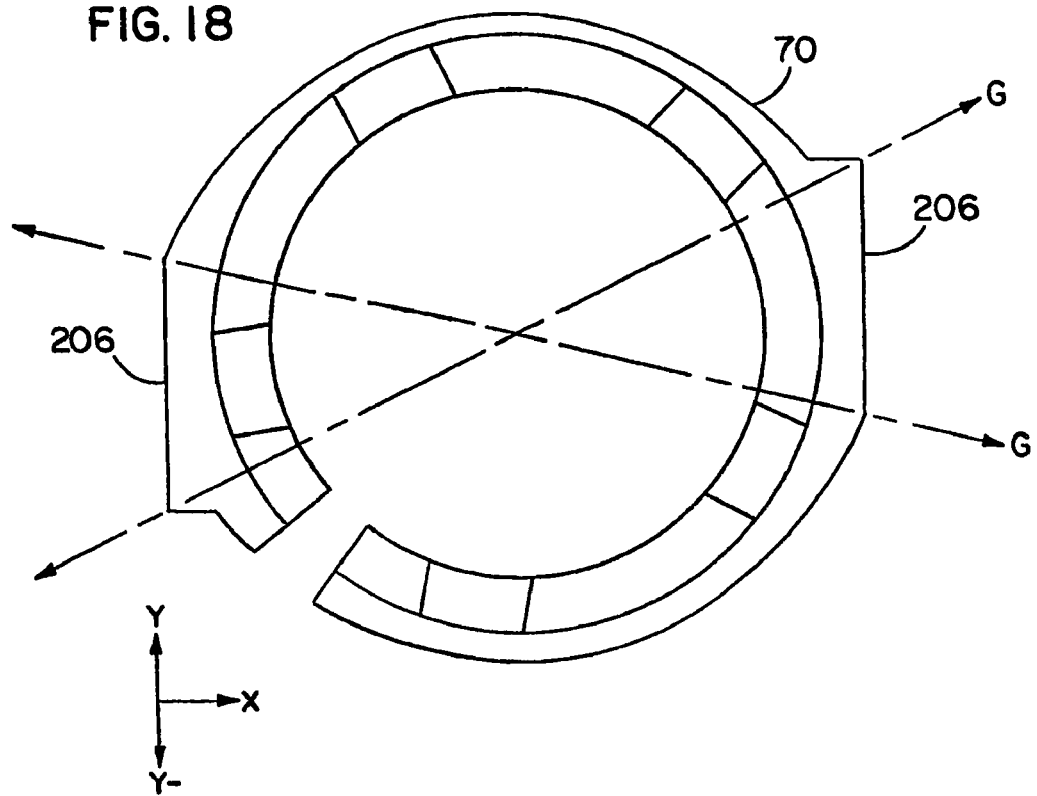
FIG. 18 is a plan view of another embodiment of a screw lock collar including features of the present invention.

A camming action locks the collar 70 within the channel 74. In a preferred form, the channel 74 has an arcuate circumferential inner surface 75, which may be non-uniform. The collar 70 also may have a varying outer diameter, such as depicted in FIGS. 7 and 18, formed by the lower step portion 108. The collar 70 may be rotated in order to compress the collar 70 within the channel 74 until reaching a locked position. The locked position may be defined by having a bump or boss within the channel beyond which the collar 70 may not rotate, or beyond which the collar 70 must rotate in order to be in a lock position but which restricts return (unlock) rotation. In addition, as depicted in FIGS. 7 and 18, the lock position may be defined by a flat 106 or 206 of the lower step portion mating with a flat 110 in the channel 74.

As illustrated in FIG. 7, the lower step 108 of the collar 70 has a first diametral dimension L1 and a second diametral dimension L2 wherein the dimension L1 is aligned with the Y (vertical) direction and dimension L2 is aligned with the X (horizontal) direction, as set by the illustrated coordinate system. In the present depiction, the gap 90 is aligned with dimension L1. However, it is preferred that the gap 90 is not positioned so as to bind with the inner surface of the channel 74 in the open or locked positions, instead being ¼.pi. radians displaced (clockwise) from the illustrated position at the L1 dimension, which is depicted in FIG. 18.

In FIG. 7, the collar 70 is oriented in a locked position with respect to the illustrated coordinate system. That is, the larger dimension L2 (versus L1) is oriented along the X axis. The screws 12, 14 are driven into the bone structure when the collar 70 is in an unlocked position, and the unlocked position of the collar 70 requires a quarter-turn (±½π radians) from the depiction of FIG. 7 so that the larger dimension L2 of the collar 70 is oriented along the Y axis. When the collar 70 is locked, the larger dimension L2 is brought to bear against the channel 74 on the interior of the bore. In order to secure the collar 70 once the screws 12, 14 are driven, the collar 70 is rotated a quarter-turn clockwise (½π radians) from the unlocked position. When rotating the collar 70 with a screw 12, 14 therein, care should be taken that the screw 12, 14 is not further rotated simultaneously, as such may be over-tightening of the screw 12, 14. As an alternative, the collar 70 and plate 10 may be configured so that the collar is locked by being rotated counter-clockwise (i.e., −½π radians), in which case the screw 12, 14 should be held in place so as to prevent loosening due to the rotation of the collar 70. In such an instance, the direction of screw back out (counter-clockwise) is in the direction of locking the collar 70.

As illustrated in FIGS. 7 and 18, the outer periphery of the lower step portion 108 of the collar 70 has a non-circular arcuate shape forming a camming surface for the collar 70. As the collar 70 is rotated, a camming action compresses the collar 70 against an interior surface of the channel 74 until the collar 70 reaches the secure or locked position when flats 106, 206 abut similarly contoured portions or flats 110 of the channel 74. Once secured, the collar 70 would have to be rotated in an opposite direction in order to undo and release the cam lock engagement to unlock the collar 70 and free the screw for intentional removal. Because of the flats 106, 206, a surgeon would have to deliberately use the tool to rotate the collar 70. As long as the collar 70 is locked, the screws 12, 14 are unable to rotate or change their orientation relative to the plate, and are unable to back-out of the bone structure.

In the preferred embodiment, a portion of the channel 74 includes a corresponding cam surface for cooperating with the cam surface on the collar 70. For example, in order for the collar 70 and the channel 74 to cam against each other, each will have a non-uniform outer dimension. Accordingly, the collar 70 has a non-uniform outer diameter with the largest diameters G at the terminal points of the flats 106, 206. (See FIGS. 7 and 18). As has been discussed, the dynamized bore 32 has a major axis providing for translation of the collar 70 therewithin. For the non-dynamized bore 34, the channel 74 has a non-uniform dimension, such as slightly oval or elliptical with major and minor axes, and has two flat portions 110 located within the channel 74 and oriented for camming against the non-uniform outer periphery of the collar 70. In the depicted embodiment, the channel 74 of the non-dynamized bore 34 has major and minor axes oriented along the Y and X axes, respectively, corresponding to the illustrated coordinate system.

Figure 11:
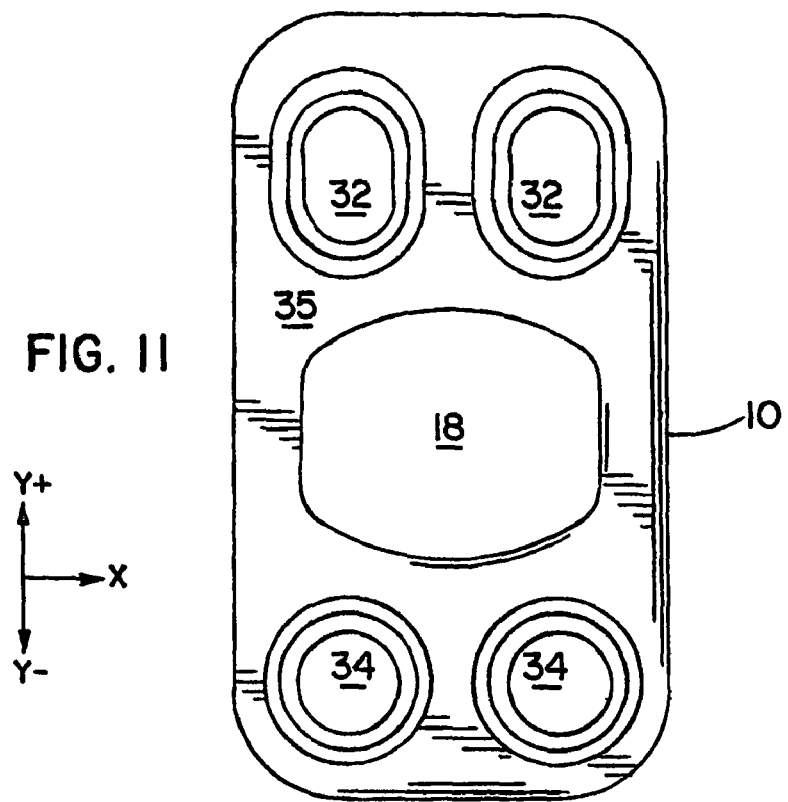
FIG. 11 is a plan view of the bone plate of FIG. 9.
Figure 12:
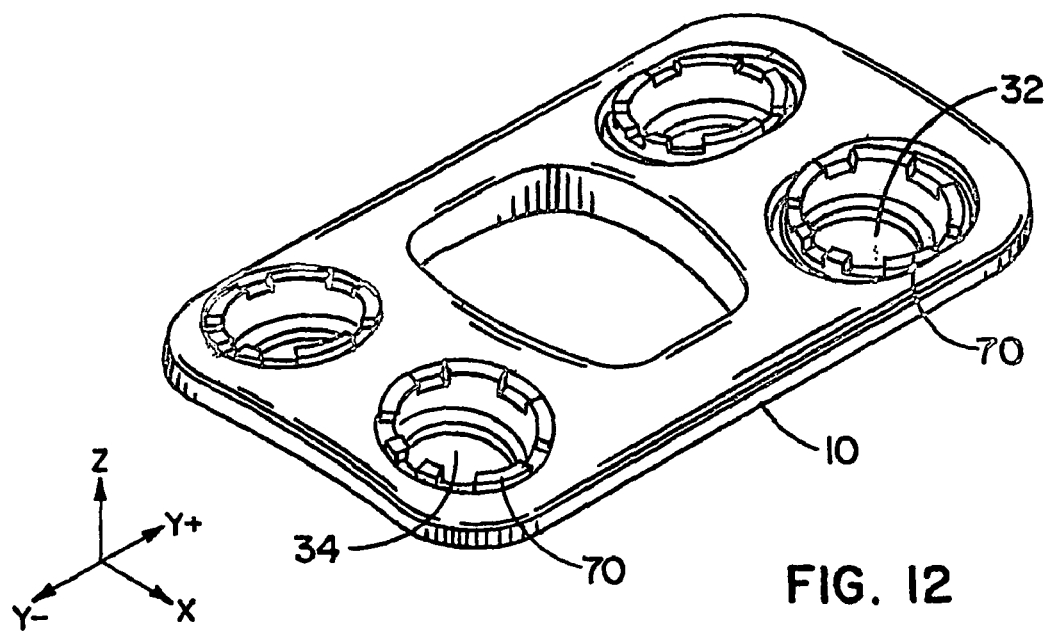
FIG. 12 is a perspective view of the bone plate of FIG. 9 with screw lock collars.
Figure 13:
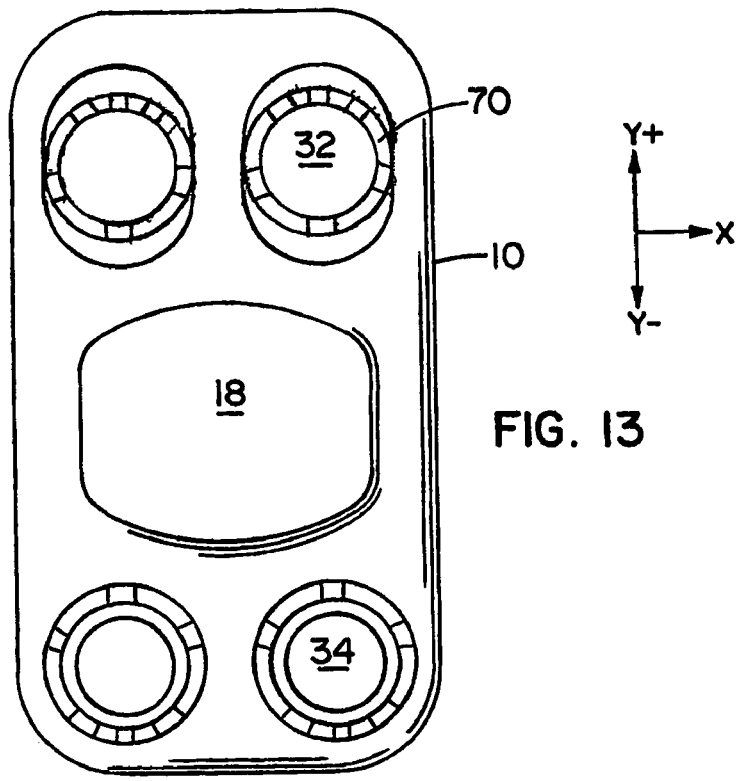
FIG. 13 is a plan elevation view of the bone plate of FIG. 9 with screw lock collars.
Figure 14:
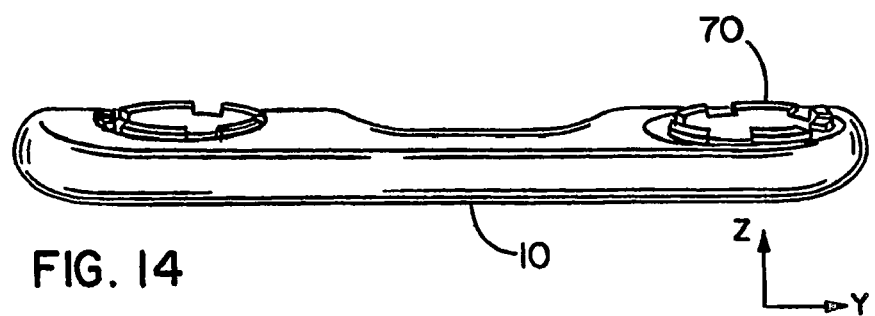
FIG. 14 is a side elevation view of the bone plate of FIG. 13 with screw lock collars.
Figure 15:
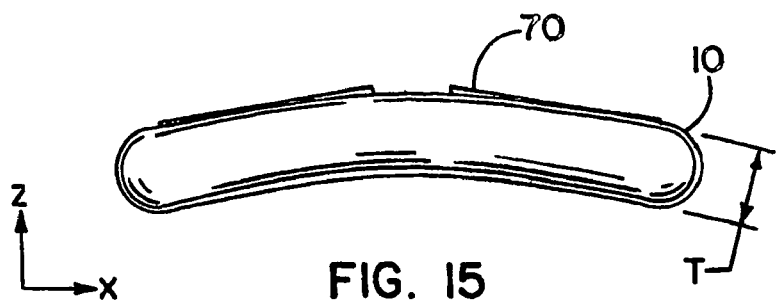
FIG. 15 is an end elevation view of the bone plate of FIG. 9 with screw lock collars.
Figure 21:
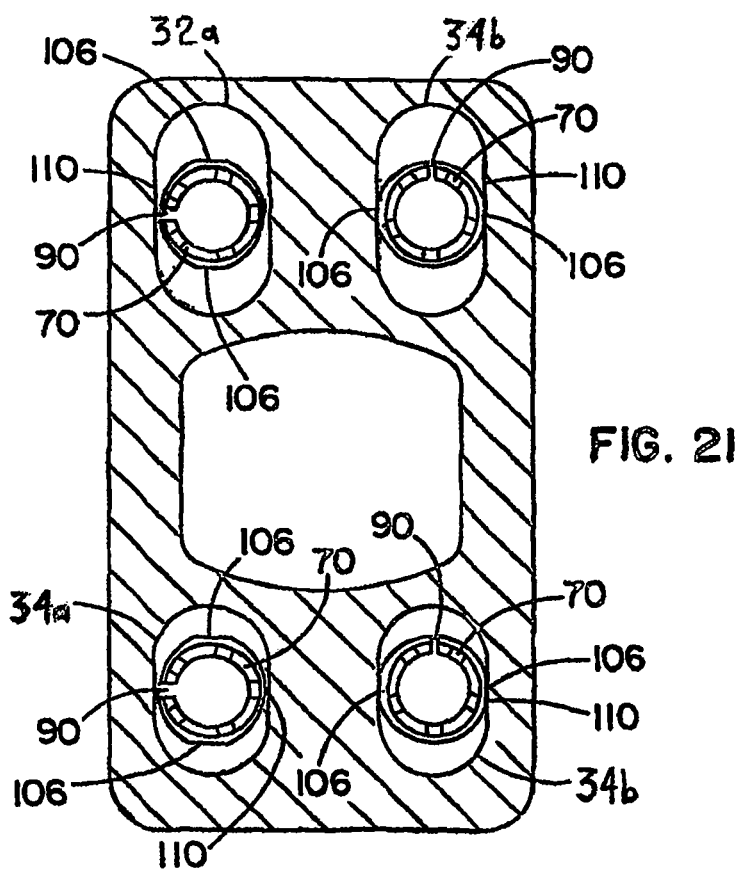
FIG. 21 is a plan cross-sectional view of the bone plate system taken along line 21-21 of FIG. 2.

With reference to figs. 11 and 21, in an unlocked state, the flats 106 of the collar 70 should be aligned with the Y axis (or at least, not aligned with the flats 110 of the channel 74, which are in the X direction). The channel 74 is sized such that the largest portion 54 of the head 50 of the screw 14 may enter the annular top 80 of the collar 70 causing expansion of the collar 70. Once the screw 14 is seated in the collar 70, the collar 70 is rotated to move the flats 106 in alignment with the flat portions 110 of the channel 74. In doing so, the diameters G and the flats 106 of the collar 70 rotate from the Y direction to the X direction, thereby camming into position where the flats 106 and flats 110 of the collar 70 and channel 74, respectively, are in engagement.

In FIG. 21, the plate 10 has a pair of dynamized bores 32 and non-dynamized bores 34 with screw lock collars 70 therein. Though the preferred plate 10 is curved, as discussed above, FIG. 21 shows a cross-section of the plate 10 in a flat plan view for simplicity. Each bore 32, 34 preferably includes the channel 74 for receiving the lower step portion 108 of the collar 70, and FIG. 21 depicts a cross-section of the plate 10 taken through the channel 74. With reference to the illustrated coordinate system, in the present embodiment, the channels 74 have a major axis along the Y axis and a minor axis along the X axis. It should be noted that the collar 70 utilized with each of the bores 32, 34 is substantially identical, and the minor axis of the channels 74 have approximately the same dimension. However, as the bore 32 provides for dynamization, the channel 74 for the dynamized bore 32 has a greater major axis than the channel 74 for the non-dynamized, fixed bore 34.

Screw lock collars 70 in bores 32a, 34a are in an unlocked position for receiving a screw, while the collars 70 in bores 32b, 34b are in a locked position for generally preventing movement of the screw relative to the collars 70. In the unlocked position, the flats 106 of the collars 70 are generally aligned along the Y axis so that the collar 70 is unlocked and the gap 90 is open. When the collar 70 moves to the locked position, the collar 70 is rotated so that the lower step portion 108 contact and cam against the flats 110 of the channel 74 until the flats 106 abut the flats 110 of the channel 74. Furthermore, locking the collar 70 causes the gap 90 to narrow.

The collar 70 locks by clamping against the head 50 of the screws 12, 14 in a radial direction in a plane orthogonal to the longitudinal axis of the screws 12, 14, and extends above and below the greatest diametral portion 54 of the head 50. Consequently, the collar 70 serves to secure the screws 12, 14 relative to the plate 10.

Figure 20:
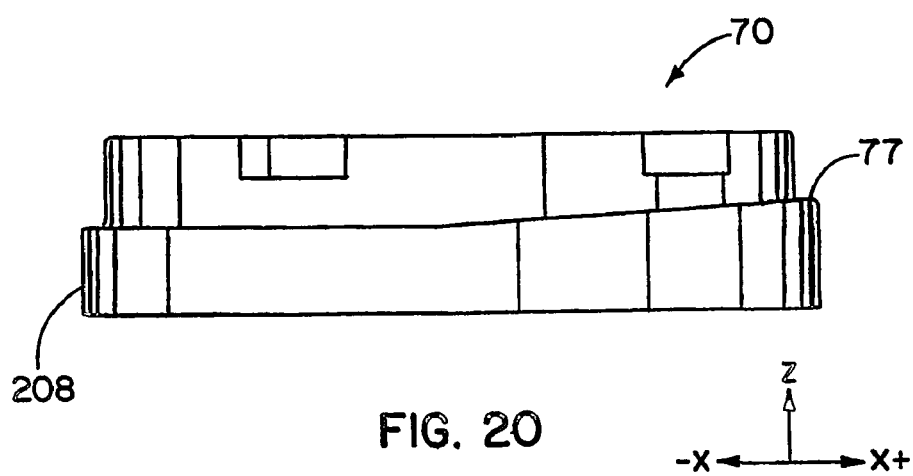
FIG. 20 is a plan view of the screw lock collar of FIG. 19.
Figure 19:
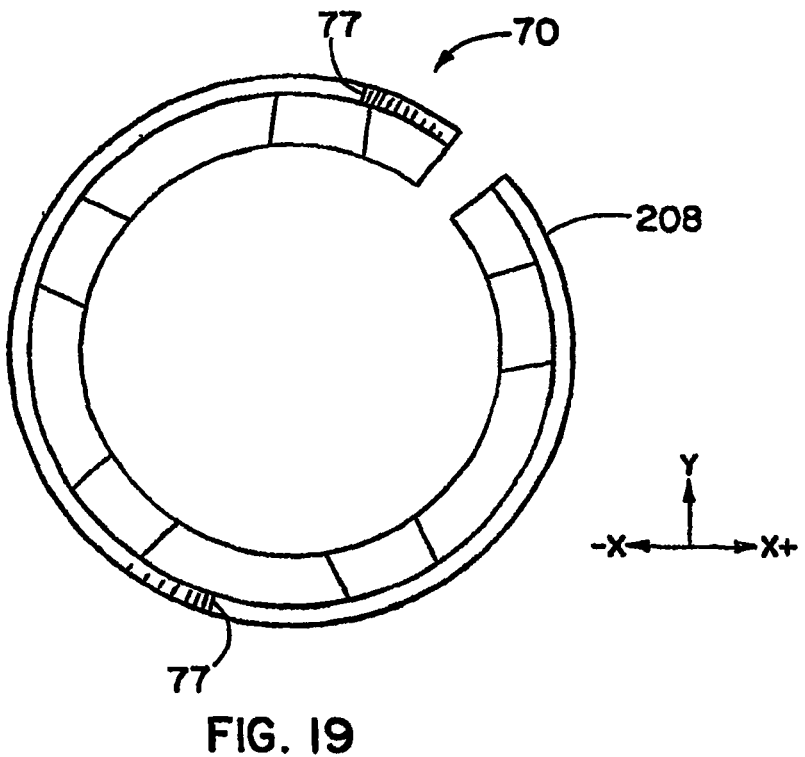
FIG. 19 is a side elevation view of another embodiment of a screw lock collar including features of the present invention.

In further embodiments of the collar 70, such as illustrated in FIGS. 19 and 20, the circumferential inner surface 75 of the channel 74 may be of uniform diameter (see FIG. 8). In one form, the height of the channel 74 may be uniform and the height of the lower step portion 208 varied. The step portion 208 has a cam surface as either a ramp or an arcuate surface 77 that leads to a flat or a valley or to a bump or boss for restricting return rotation. In another form, the height of the channel 74 may have a corresponding cam surface that mates with the above described cam surface 77 of the step portion 208.

As discussed earlier, the dynamized screws 12 are inserted in dynamized bores 32. That is, the bores 32 generally have major and minor axes to allow the compressive force of gravity to shorten the distance between the screws 12 in one bone or vertebra and the screws 14 in another bone or vertebra. Accordingly, the elongated channels 74 providing for the vertical movement of the dynamized screws 12 also allow the locked collar 70 to move therewith. Therefore, the geometry of the channels 74 that are provided for non-dynamized screws 14 is generally replicated but with a greater vertical (Y direction) length provided for the elongated channels 74 of the dynamized screws 12. Therefore, the same camming action is provided for the collars 74 of the screws 12 and screws 14 while also providing dynamization. In order to permit the proper motion of dynamization without affecting the tightened screws, the mating surfaces between the collars 70 and the screws 12 are provided with a greater coefficient of friction (and concomitant greater frictional force) than are the mating surfaces of the collar 70 and plate 10. Thus, the collar 70 may slide against the plate 10 as the screws compress, but the collar 70 does not rotate relative to the screws 12, 14.

As also discussed above, the movement of the dynamized screws 12 in the dynamized bores 32 should not affect the orientation of the screws 12 relative to the plate 10. That is, when vertebral sections compress, these sections should do so generally linearly along the spine. If the compression is not linear, the vertebral sections will move out of proper alignment, which can lead to undesired pressure on the nervous system portion of the spinal column, with uneven pressure on the end plates of the vertebral sections themselves, with incorrect healing by graft material, and with pressure on the plate 10 and the screws 12, 14 themselves. The screws 12, 14 used herein are preferably polyaxial, the shank 40 of each having a diameter smaller than the diameter of the head 50. Without locking the polyaxial screw in its proper orientation once driven, the polyaxial screw would be permitted to change its orientation relative to the plate when allowed to move in a dynamized hole. Accordingly, the screw locks, such as the collar 70, allows the polyaxial screws to be driven in a desired orientation relative to the plate, and then to be locked in that orientation by locking the screw locks 70. As the screw locks for the dynamized bores follow a precise linear path, the orientation of the locked dynamized screws is not altered when the vertebral sections compress.

In order to simplify the procedure for the surgeon, it is preferred to provide assistance to the surgeon in rotating the collar 70 the proper amount. As stated above, the gap 96 is oriented ¼π radians from that depicted in FIG. 7. However, in an alternative embodiment, the gap 96 may be utilized as depicted so that a surgeon may visually identify when the gap 96 is aligned and, thus, recognize the proper amount of rotation of the collar 70 itself. As another alternative, there may be a stop or bump (not shown) or other feature provided within or in close proximity to the channel or elsewhere that prevents over-rotation of the collar 70. If the surgeon were to over-rotate the collar 70, the collar 70 (and, hence, the screw 12, 14) would not be in the preferred, secured position.

The configuration of the embodiment as depicted is simply one configuration, specifically a configuration for two vertebrae during a vertebral fusion operation. However, other configurations maybe utilized for the plate 10 such as in the contour (arched profile in the Z direction), and the number of screws and bores. The plate 10 may also be configured for securing any number of bones, such as three vertebrae or multiple fracture portions of a large bone such as the femur. Dynamization may be omitted in the case where gravitational compression is not available. Forms of the plate 10 may be utilized with compression screw slots or holes. As another alternative, dynamization may be utilized where a secondary or external means of compression once the screws are driven, for instance before the collars are locked. The material used for the plate should be bio-compatible for implantation, and it is preferred that the material of the plate 10 is as radiolucent as possible, such as a titanium-based material, so that X-rays may be utilized to provide a doctor or medical personnel with the ability to see the fusion site without the plate 10 obscuring or hiding the view. As a further alternative, the collar 70 may include a groove or recess for receiving a protrusion or ramp or cam located on the interior surface of the collar bores such that the collar 70 and bores are in a camming engagement for compressing the head of the bone screws 12, 14.

While the invention has been described with respect to specific examples including presently preferred modes of carrying out the invention, those skilled in the art will appreciate that there are numerous variations and permutations of the above described systems and techniques that fall within the spirit and scope of the invention.

The invention claimed is:

1. A device for stabilization of adjacent vertebrae of a spine, the device comprising:
    a bone plate;
    a plurality of bores in the bone plate;
    a bone anchor configured for extending through one of the bores;
    a head of the bone anchor having a spherical outer surface and a shank depending from the head;
    a pair of spaced, flat portions of the one bore that extend substantially parallel to one another and which are spaced by a predetermined fixed distance;
    a rotary anchor lock collar member extending about a central axis for being rotatably received in the one bore;
    a curved inner surface of the rotary anchor lock collar member adapted to engage the spherical outer surface of the head of the bone anchor to permit the bone anchor to be rotationally driven through the one bore along one of a plurality of different driving axes that are transverse to the central axis and into a vertebral bone;
    an upper portion of the rotary anchor lock collar member having notches spaced circumferentially thereabout for receiving a driving tool therein to rotate the rotary anchor lock collar member in the one bore;
    a lower portion of the rotary anchor lock collar member having a split-ring construction so that the anchor lock lower portion has facing circumferential ends that are spaced apart from one another by a gap therebetween;
    a larger dimension and a smaller dimension of the rotary anchor lock lower portion having respective axes that extend through the center of the split ring rotary anchor lock collar member substantially orthogonal to each other with the larger dimension being greater than the predetermined fixed distance and the smaller dimension being less than the predetermined fixed distance; and
    cooperating inner and outer surfaces of the one bore flat portions and the anchor lock lower portion respectively, which cause the facing ends to shift toward each other with approximately ninety degrees of rotation of the anchor lock collar member, after the bone anchor has been driven through the one bore and into the vertebral bone, so that rotation of the rotary anchor lock collar member is independent from the rotational driving of the bone anchor with the rotating anchor lock collar member being rotated from an open, bone anchor receiving configuration with the larger dimension axis oriented to be substantially parallel to the bore flat portions to a clamped, bone anchor locking configuration with the larger dimension axis oriented to be substantially perpendicular to the bore flat portions to cause the facing ends to shift toward each other to reduce the size of the gap therebetween so that the bone anchor extending through the one bore and the rotary anchor lock collar member therein is locked in the one bore against back out therefrom and against polyaxial movement relative to the bone plate and the rotary anchor lock collar member.

2. The device of claim 1 wherein the rotary anchor lock lower portion includes two substantially flat surfaces that are diametrically opposed to one another along the larger dimension axis and each abut a bore flat portion when the rotary anchor lock collar member is in the clamped, bone anchor locking configuration to resist anchor lock rotation away from the bone anchor locking configuration.

3. The device of claim 2 wherein each substantially flat surface is adjacent an anchor lock camming surface so that when the rotary anchor lock collar member is rotated between the bone anchor receiving and locking configurations, the transition between the anchor lock camming surfaces camming against the bore flat portions and the anchor lock substantially flat surfaces abutting the bore flat portions provides tactile feedback to a surgeon that the anchor lock has been shifted to the locking configuration.

4. The device of claim 1 wherein the facing circumferential ends are oriented on the rotary anchor lock collar member in a position that generally avoids contact with the bore flat portions so as to minimize hang-ups when the anchor lock is rotated between bone anchor receiving and locking configurations.

5. The device of claim 1 wherein the gap is positioned in a predetermined location when the anchor lock collar member is shifted to the bone anchor locking configuration to allow a surgeon to visually recognize when the anchor lock has been rotated to the locking configuration.

6. The device of claim 1 wherein the bone plate is one of a titanium, stainless steel, and PEEK material.

7. A device for stabilization of adjacent vertebrae of a spine, the device comprising:
    a bone plate;
    a plurality of bores in the bone plate configured to each receive a bone screw extending therethrough;
    at least one of the bores being a dynamized bore having an elongate configuration to allow a bone screw extending therethrough and into a vertebral bone to shift relative to the bone plate;
    a pair of opposed flat portions of the dynamized bore which extend along the length thereof;
    a screw lock member configured to be rotatably received in the dynamized bore for being rotated between a screw receiving unlocked configuration and a screw locking configuration;
    a pair of diametrically opposed outer flats of the screw lock member which have a planar configuration, the flats facing radially outward from the screw lock member and extending parallel to one another; and
    a substantially smooth inner surface of the screw lock member having an inner diameter sized in clearance with the bone screw when in the screw receiving unlocked configuration, wherein rotation of the screw lock member to the screw locking configuration brings the flats into confronting relation with the opposed bore flat portions which substantially uniformly reduces the inner diameter in size so that the smooth inner surface provides a uniform clamping force about the bone screw and the flats are configured to slide along the bore flat portions to permit relative translation of the bone screw and the screw lock member in the dynamized bore while the confronting engagement of the flats of the screw lock member against the flat portions of the dynamized bore avoids turning of the screw lock member of the dynamized bore as the screw lock member slides along the bore flat portions to keep the screw lock member in the screw locking configuration for resisting back out of the bone screw from the dynamized bore.

8. The device of claim 7 wherein the rotatable screw lock member has a larger dimension and a smaller dimension, the larger dimension being brought to bear against the bore flat portions upon rotation of the screw lock member from the screw receiving configuration to the screw locking configuration which shortens the larger dimension and causes the screw lock member to constrict about the bone screw.

9. The device of claim 8 wherein the dynamized bore has both minor and major axes and the larger dimension of the screw lock member is aligned with the major axis of the bore when the screw lock member is in the screw receiving configuration and the minor axis when the screw lock member is in the screw locking configuration.

10. The device of claim 8 wherein the substantially smooth inner surface of the screw lock member conforms to a corresponding surface on the bone screw, the screw lock member inner surface and the corresponding surface on the bone screw having a greater coefficient of friction than a coefficient of friction between the flats of the screw lock member and the bore flat portions to permit dynamization of the rotatable screw lock member within the bore without loosening engagement of the screw lock member about the bone screw.

11. The device of claim 7 wherein the screw lock member includes outer curved surfaces and junctures between the curved surfaces and the flats, the junctures being diametrically opposed across the screw lock member with the largest diameter of the screw lock member being between the diametrically opposed junctures.

12. A bone plate system for securing a plurality of bones in a desired alignment, the bone plate system comprising:
  a bone plate having a top surface and a bottom surface;
  a plurality of bores extending through the plate which receive bone anchors for securing the plate to the plurality of bones;
  a channel of one of the bores, the channel being located between the top and bottom surfaces of the plate and having upper and lower surfaces extending radially outward from the bore;
  a split ring locking collar configured for being rotatably received in the one bore;
  a radially outer step portion of the locking collar having a thicker portion and a thinner portion extending about the circumference of the step portion, the thicker portion being continuous about the circumference and the thinner portion being interrupted by the split in the split ring locking collar; and
  an upwardly facing cam surface extending between the thicker and thinner portions of the locking collar step portion configured for camming against the channel upper surface so that rotation of the locking collar toward a locked configuration thereof brings the locking collar cam surface into engagement with the channel upper surface which causes a tight wedge fit of the step portion thicker portion in the channel to avoid reverse rotation back toward an unlocked configuration of the collar in the bore.

13. The bone plate system of claim 12 wherein the upwardly facing cam surface of the locking collar is a ramp disposed between the thicker and thinner portions of the locking collar.

14. The bone plate system of claim 12 wherein the thicker portion of the locking collar has a projection that mates with the channel upper surface to restrict return rotation of the locking collar.

* * * * *